(12) United States Patent
Vander Lind et al.

(10) Patent No.: US 9,353,033 B2
(45) Date of Patent: May 31, 2016

(54) AIRBORNE RIGID KITE WITH ON-BOARD POWER PLANT FOR SHIP PROPULSION

(71) Applicant: Google Inc., Mountain View, CA (US)

(72) Inventors: Damon Vander Lind, Alameda, CA (US); Thomas Van Alsenoy, Oakland, CA (US); Richard Wayne DeVaul, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/485,412

(22) Filed: Sep. 12, 2014

(65) Prior Publication Data

US 2015/0298806 A1    Oct. 22, 2015

Related U.S. Application Data

(60) Provisional application No. 61/981,050, filed on Apr. 17, 2014.

(51) Int. Cl.
*F02B 63/04* (2006.01)
*F03G 7/08* (2006.01)
(Continued)

(52) U.S. Cl.
CPC ............ *C07C 29/141* (2013.01); *B63H 9/0685* (2013.01); *B64C 31/06* (2013.01);
(Continued)

(58) Field of Classification Search
CPC ...................... B63H 9/0685; B63H 2009/0692; F05B 2240/921; F05B 2240/93; F05B 2240/95; F03D 5/00; F03D 5/02; F03D 5/04; F03D 5/06; F03D 9/008
USPC ........................................ 290/1 R, 44, 54, 55
See application file for complete search history.

(56) References Cited

U.S. PATENT DOCUMENTS

| 4,282,187 A | 8/1981 | Corbell et al. |
| 4,568,522 A | 2/1986 | Corbell |

(Continued)

FOREIGN PATENT DOCUMENTS

| CA | 2763225 | 7/2011 |
| EP | 2698312 | 2/2014 |
| JP | 2013-508218 | 3/2013 |

OTHER PUBLICATIONS

Eisaman et al., "C02 extraction from seawater using bipolar membrane electrodialysis," Energy & Environmental Science, 2012, vol. 5, pp. 7346-7352.

(Continued)

*Primary Examiner* — Tulsidas C Patel
*Assistant Examiner* — Thomas Quigley
(74) *Attorney, Agent, or Firm* — McDonnell Boehnen Hulbert & Berghoff LLP.

(57) ABSTRACT

A vehicle-based airborne wind turbine system having an aerial wing, a plurality of rotors each having a plurality of rotatable blades positioned on the aerial wing, an electrically conductive tether secured to the aerial wing and secured to a ground station positioned on a vehicle, wherein the aerial wing is adapted to receive electrical power from the vehicle that is delivered to the aerial wing through the electrically conductive tether; wherein the aerial wing is adapted to operate in a flying mode to harness wind energy to provide a first pulling force through the tether to pull the vehicle; and wherein the aerial wing is also adapted to operate in a powered flying mode wherein the rotors may be powered so that the turbine blades serve as thrust-generating propellers to provide a second pulling force through the tether to pull the vehicle.

27 Claims, 11 Drawing Sheets

(51) Int. Cl.
- *H02K 7/18* (2006.01)
- *C07C 29/141* (2006.01)
- *F03D 9/00* (2016.01)
- *B63H 9/06* (2006.01)
- *B64C 31/06* (2006.01)
- *F03D 5/00* (2006.01)

(52) U.S. Cl.
CPC .............. *F03D 5/00* (2013.01); *F03D 9/002* (2013.01); *F05B 2240/917* (2013.01); *F05B 2240/921* (2013.01); *Y02E 10/70* (2013.01); *Y02E 10/725* (2013.01); *Y02E 10/728* (2013.01)

(56) References Cited

U.S. PATENT DOCUMENTS

| | | | | |
|---|---|---|---|---|
| 5,435,259 | A * | 7/1995 | Labrador | 114/39.31 |
| 6,113,773 | A | 9/2000 | Shimamune et al. | |
| 7,129,596 | B2 | 10/2006 | Macedo | |
| 8,080,889 | B2 | 12/2011 | Ippolito et al. | |
| 8,277,632 | B2 | 10/2012 | Murahara | |
| 8,350,403 | B2 | 1/2013 | Carroll | |
| 8,575,770 | B2 | 11/2013 | Devine | |
| 2007/0176432 | A1* | 8/2007 | Rolt | 290/55 |
| 2007/0250226 | A1* | 10/2007 | Wrage | B63H 9/0685 701/21 |
| 2009/0221725 | A1 | 9/2009 | Chornet et al. | |
| 2010/0244450 | A1 | 9/2010 | Tabe | |
| 2011/0101692 | A1 | 5/2011 | Bilaniuk | |
| 2011/0260462 | A1 | 10/2011 | Vander Lind | |
| 2012/0104763 | A1 | 5/2012 | Lind | |
| 2013/0008792 | A1 | 1/2013 | Eisaman et al. | |
| 2013/0193266 | A1 | 8/2013 | Dimarzio et al. | |
| 2013/0213289 | A1 | 8/2013 | Borden et al. | |
| 2013/0221679 | A1 | 8/2013 | Vander Lind | |
| 2013/0307274 | A1 | 11/2013 | Sia | |

OTHER PUBLICATIONS

Graves, Christopher Ronald, "Recycling C02 into Sustainable Hydrocarbon Fuels: Electrolysis of C02 and H20," submitted in partial fulfillment of the requirements for the degree of Doctor of Philosophy in the Graduate School of Arts and Sciences; Columbia University, 2010, 282 pages.
Pickering, Keith, "Seawater+ electricity= jet fuel," published on the website: Daily Kos, Kos Media, LLC, Jan. 18, 2013, 7 pages.
Jiang, Z. et al., "Turning carbon dioxide into fuel," Phil. Trans. R. Soc. A, 2010, vol. 368, pp. 3343-3364.
Holte, Laura L. et al., "Sustainable Transportation Fuels From Off-Peak Wind Energy, C02, and Water," ASME 2010 4th International Conference on Energy Sustainability, May 17, 22, 2010, Phoenix, AZ USA, American Society of Mechanical Engineers, pp. 795-801.
http://parc.com/publication/2837/co2-extraction-from-seawater-using-bipolar-membrane-electrod ialysis.html, 1 page.
International Searching Authority, International Search Report mailed Jul. 24, 2015, issued in connection with International Application No. PCT/US2015/025553, 2 pages.
DeVaul et al., U.S. Appl. No. 14/224,021, filed Mar. 24, 2014, 41 pages.

* cited by examiner

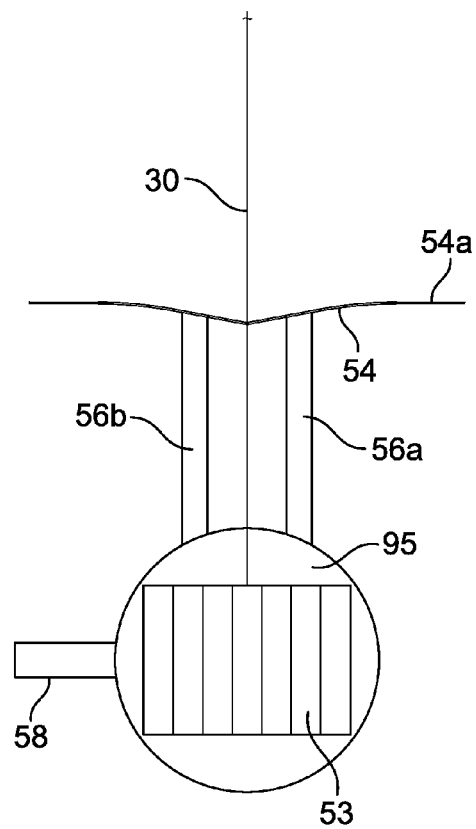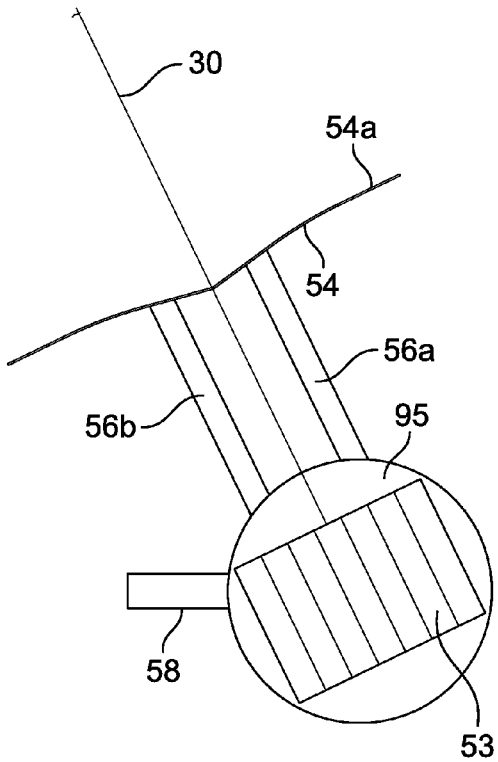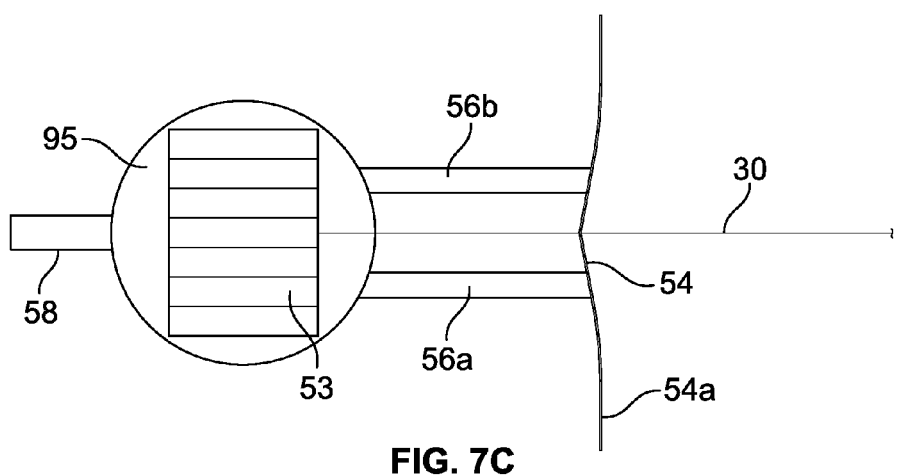
FIG. 7A
FIG. 7B
FIG. 7C

AIRBORNE RIGID KITE WITH ON-BOARD POWER PLANT FOR SHIP PROPULSION

This Application claims priority to U.S. Provisional Patent Application No. 61/981,050 entitled "Airborne Rigid Kite With On-Board Power Plant For Ship Propulsion" filed on Apr. 17, 2014, the contents of which is incorporated by reference in its entirety.

BACKGROUND

Unless otherwise indicated herein, the materials described in this section are not prior art to the claims in this application and are not admitted to be prior art by inclusion in this section.

Power generation systems may convert chemical and/or mechanical energy (e.g., kinetic energy) to electrical energy for various applications, such as utility systems. As one example, a wind energy system may convert kinetic wind energy to electrical energy.

SUMMARY

A vehicle-based airborne wind turbine system capable of pulling a ship is provided. The system include an aerial wing having a plurality of rotors each having rotatable blades positioned on the wing. The aerial wing is attached to a ground station positioned on the ship with an electrically conductive tether. The aerial wing is adapted to operate in a flying mode where wind energy is harnessed by the wing during flight and a pulling force is directed through the tether to the ship. The aerial wing is also adapted to operate in a powered flying mode where the rotors are powered to rotate the blades that serve as thrust-generating propellers to provide additional pulling force to pull the ship. The aerial wing may also operate in a power generation mode during the flying mode or powered flying mode where air moving across the rotatable blades of one or more of the rotors forces them to rotate, thereby driving a generator to produce electrical energy.

In another aspect, a vehicle-based airborne wind turbine system is provided having an aerial wing, a plurality of rotors each having a plurality of rotatable blades positioned on the aerial wing, an electrically conductive secured to the aerial wing and to a ground station positioned on a vehicle, wherein the aerial wing is adapted to receive electrical power from the vehicle that is delivered through the electrically conductive tether, wherein the aerial wing is adapted to operate in a flying mode to harness wind energy to provide a first pulling force through the tether to pull the vehicle, and wherein the aerial wing is also adapted to operate in a powered flying mode wherein the rotors may be powered so that the turbine blades serve as thrust-generating propellers to provide a second pulling force through the tether to pull the vehicle.

In another aspect, an airborne wind turbine system is provided having an aerial wing, a plurality of rotors each having a plurality of rotatable blades positioned on the aerial wing, an electrically conductive tether having a first end secured to the aerial wing and a second end secured to a ground station positionable on a vehicle, wherein the aerial wing is adapted to receive electrical power from the vehicle that is delivered to the aerial wing through the electrically conductive tether, wherein the aerial wing is adapted to operate in a flying mode to harness wind energy to provide a first pulling force through the tether to pull the vehicle, and wherein the aerial wing is also adapted to operate in a powered flying mode wherein the rotors may be powered so that the turbine blades serve as thrust-generating propellers to provide a second pulling force through the tether to pull the vehicle.

In a further aspect, a method of pulling a vehicle is provided including the steps of providing an aerial wing, and a plurality of rotors each having a plurality of rotatable blades positioned on the aerial wing, and having an electrically conductive tether having a first end secured to the aerial wing and a second end secured to a ground station positioned on a vehicle, wherein the aerial wing is adapted to receive electrical power from the vehicle that is delivered to the aerial wing through the electrically conductive tether; wherein the aerial wing is adapted to operate in a flying mode to harness wind energy to provide a first pulling force through the tether to pull the vehicle; and wherein the aerial wing is also adapted to operate in a powered flying mode wherein the rotors are be powered so that the turbine blades serve as thrust-generating propellers to provide a second pulling force through the tether to pull the vehicle, and operating the aerial wing in the powered flying mode to provide a pulling force through the tether to pull the vehicle.

In a further aspect, means for pulling a vehicle are provided.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7A is a top view of the perch platform 95 with tether 30 extending from rotatable drum 53 with perch platform 95 in a first position relative to extending arm 58 of the perch platform 95, according to an example embodiment.

FIG. 7B is a top view of the perch platform 95 shown in FIG. 7A with tether 30 extending from rotatable drum 53 with perch platform 95 in a second position relative to extending arm 58 of the perch platform 95, according to an example embodiment.

FIG. 7C is a top view of the perch platform 95 shown in FIGS. 7A-7B with tether 30 extending from rotatable drum 53 with perch platform 95 in a third position relative to extendable arm 58 of the perch platform 95, according to an example embodiment.

DETAILED DESCRIPTION

Figure 1:
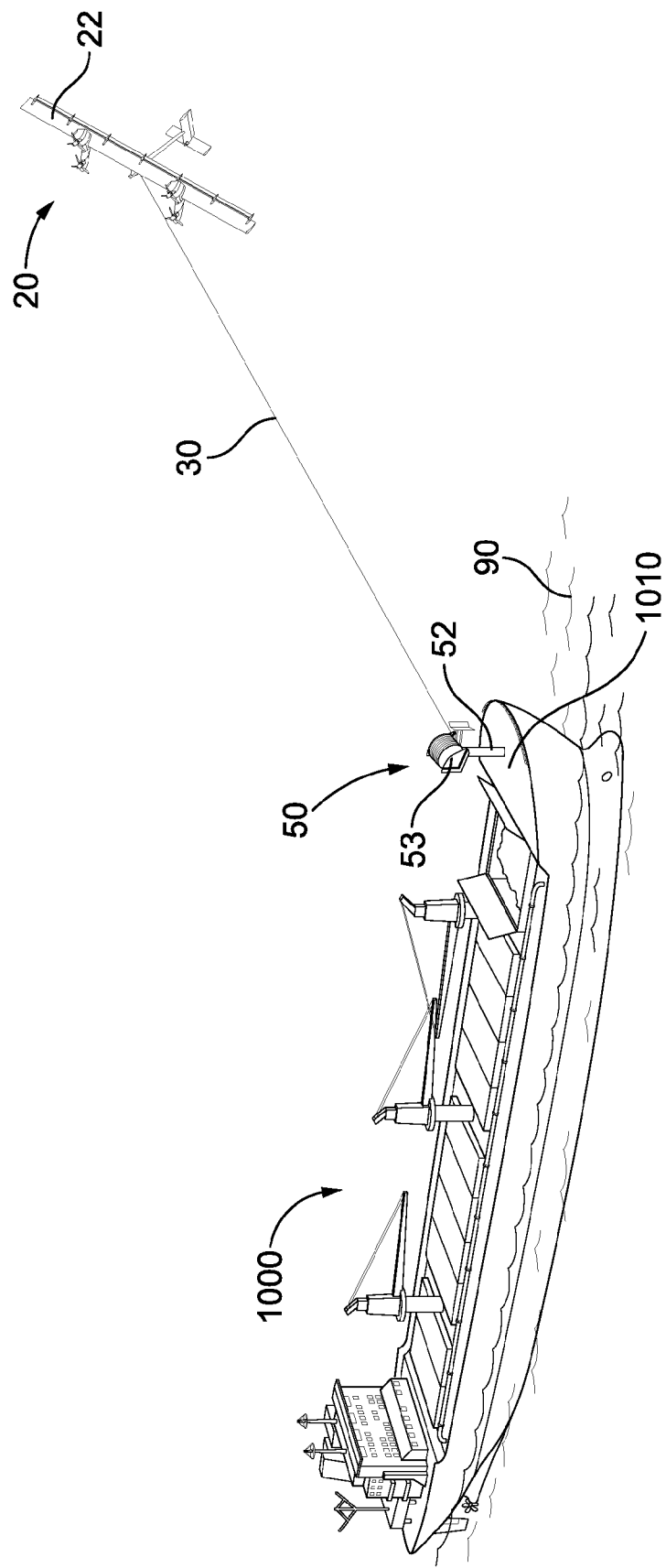
FIG. 1 is a perspective view of airborne wind turbine 10 including aerial vehicle 20 attached to a ship 1000 with an electrically conductive tether 30, according to an example embodiment.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

1. Overview

Ships have been used to transport products for centuries. Historically, ships were equipped with sails to harness wind energy to propel the ship. More recently, wind powered ships have given way to large modern cargo ships propelled by underwater propellers driven by fuel powered engines. The use of a traditional sail system on a modern cargo ship is often not feasible due to the large physical size required for such a sail system given that the propulsion requirements for a modern cargo ship are often in the megawatt range. Additionally, the unpredictable nature of wind resources is often not attractive for cargo ships because allocated timeslots in ports often require strict adherence to scheduled arrival times. Thus, conventional sail systems to harness wind energy are not typically used with modern cargo ships.

Instead, modern cargo ships are typically propelled using one or more underwater propellers that are driven by a fuel powered engine. However, a typical modern cargo ship has the drawbacks of having high fuel costs and the potentially adverse environmental impact based on the use of fossil fuels to provide ship propulsion.

The use of wind turbines as a means for harnessing energy has been used for a number of years. Conventional wind turbines typically include large turbine blades positioned atop a tower. An alternative to the costly conventional wind turbine towers that may be used to harness wind energy is to use an aerial vehicle attached to a ground station with an electrically conductive tether. Such an alternative may be referred to as an Airborne Wind Turbine or "AWT."

An AWT is a wind based energy generation device that includes an aerial vehicle constructed of a rigid wing with mounted turbines that flies in a path, such as a substantially circular path, across the wind at, for example, between 250 and 600 meters above the ground (or water) to convert kinetic wind energy to electrical energy. The aerial vehicle is attached to a ground station via an electrically conductive tether. In the cross wind flight, the aerial vehicle may fly across the wind in a circular pattern similar to the tip of a wind turbine. The rotors attached to the rigid wing may be used to generate power. In the power generating mode, air moving across the turbine blades forces them to rotate, driving a generator to produce electricity. The aerial vehicle is typically connected to a ground station via an electrically conductive tether that transmits power generated by the aerial vehicle to the ground station, where it may be used for various purposes, including powering the aerial vehicle or other auxiliary purposes.

The aerial vehicle may be parked on a perch positioned with the ground station when not in use, for example during poor weather conditions. In some embodiments, when parked, the aerial vehicle may be perched in an upward position with the axis of the fuselage positioned generally perpendicular to the ground. When it is time to launch the aerial vehicle, the rotors may be operated in a thrust generating mode, where the rotors may be powered so that the turbine blades serve as thrust-generating propellers.

During launch, the aerial vehicle may operate in a hover mode, with the fuselage generally perpendicular to the ground (i.e., less than 45 degrees away from vertical), the rotors may operate in the thrust generating mode, where the thrust-generating propellers power the aerial vehicle to a desired height. In some embodiments, the power to rotate the turbine blades in the thrust generating mode is provided through the electrically conductive tether from the ground station, and in other embodiments the power to rotate the turbine blades is supplied from power stored on the aerial vehicle.

When a desired height is attained, the aerial vehicle may transition from a hover mode to a cross-wind flight or flying mode, and operate in the power generation mode. During cross-wind flight, the aerial vehicle may fly cross-wind in a substantially circular path. When it is desired to land the aerial vehicle, such as during inclement weather, the electrically conductive tether is wound onto a spool or drum in the ground station and the aerial vehicle is reeled in towards a perch on the ground station. Prior to landing on the perch, the aerial vehicle transitions from a flying mode to a hover mode. The drum is further rotated to further wind the tether onto the drum until the aerial vehicle eventually comes to rest on the perch.

A drum may be used to store the tether as it is reeled in towards the ground station during a landing procedure. In an example embodiment, the drum may rotate about horizontal axis. The platform may include a perch that extends from ground station and includes perch supports. In some embodiments, the perch and perch supports may rotate about the top of the ground station to allow for a desired positioning of the perch during landing and launch.

Example embodiments are directed to an airborne wind turbine system positioned on a cargo ship, or other seagoing vessel. It is known that airborne wind turbines may fly at a distance of 500 meters above the ground where the wind is significantly stronger than closer to the ground (e.g. 70 meters). The wind at 500 meters may provide twice the power as wind at 70 meters. Furthermore, strong, consistent winds may be found in offshore locations.

Example embodiments are directed to an airborne wind turbine system that may be positioned on the cargo ship or seagoing vessel where an aerial vehicle is attached by an electrically conductive tether that extends from the aerial vehicle to a ground station located on the ship. The aerial vehicle may be used to tow the cargo ship or other vessel by harnessing wind energy during cross wind flight and/or by propelling the aerial vehicle forward with its onboard propellers.

In particular, the present embodiments are directed to the use of a rigid airborne, powered, tethered craft (referred to as an aerial wing hereafter) for ship propulsion. The airborne wind turbine system may be the same as that described above that is used on a ground-based airborne wind turbine system. The airborne wind turbine may include an aerial wing having an aerodynamic surface designed to be propelled by the wind using the crosswind principle in a flying mode, and a power plant mounted on the aerial wing consisting of rotors having propellers, electric motors and motor controllers. The power plant is capable of both generating thrust (thrust generating mode) to tow the ship and also of generating drag to generate electricity (power generating mode) that may be transferred to the ground station or stored on the aerial wing for later use. The airborne turbine system may include an electrically conductive cable or tether capable of transferring the generated tension to an anchor point on the ship and capable of transferring electric power to and from the power plant on the aerial vehicle. The airborne turbine system may also include an anchor point on the ship capable of transferring the tether tension in the ship hull, as well as active autonomous control which maintains the aerial wing on a predefined, stable trajectory.

When installed on a vessel, the following modes of operation may be used:

(a) Under good wind conditions, the aerial wing is propelled by the wind during cross wind flight in a flying mode, thereby generating tension in the tether and thereby pulling or towing the ship forward.

(b) Under very favorable wind conditions, the onboard power plant slows the aerial wing down by absorbing part of the wind energy and operating in power generation mode while in flying mode, or power generation mode. This mode of operation results in pulling or towing power identical to (a) and the conversion of wind energy to electrical energy which may be transferred through the electrically conductive tether to the ship where it may be used or stored on the vessel for either propulsive or auxiliary purposes, or used or stored on the aerial wing for either propulsive or auxiliary purposes.

(c) Under fair wind conditions, electric energy stored or generated on the vessel (battery bank, main engine with generator or auxiliary generator), or stored on the aerial wing, can be delivered to the power plant on the aerial wing through the electrically conductive tether to operate the aerial wing in thrust generating mode while in the flying mode (hereinafter referred to as powered flying mode). In this mode of operation, the energy may be used to power the propellers on the aerial vehicle, thereby providing an additional pulling force that generates tension in addition to the pulling force as in (a).

As long as there is a component of the true wind speed in the travel direction of the vessel, the net propulsive efficiency using this powered flying mode is higher compared to a marine propeller referencing against water. Although electric energy is consumed in this mode, the propulsive efficiency is significantly higher than using a marine propeller. Under certain conditions, the net efficiency (electric power in/propulsive power out) can be on the order of 200%-300%. This can be achieved because the system is still extracting energy from the available wind field while operating in the powered flying mode, thus the pulling force of the harnessed wind from the flying mode is combined with the pulling force from the rotating blades of the rotors.

It will be appreciated that the powered flying mode of operation may also be used during many different types of wind conditions, including the fair, good, and very favorable conditions referred to above. Further, during the flying mode of operation, power may be supplied to the rotors to provide for steering and control purposes.

In some embodiments, the aerial wing could have some rotors operating in power generating mode, and others operating in powered flight mode, in which case the aerial wing may operate in both power generation mode and powered flying mode at the same time.

Under unfavorable wind conditions, the aerial wing may be reeled in and perched or parked on the ground station.

The aerial wing embodiments provide significant advantages over a non-powered kite system. In particular, in non-powered kite systems, there is a narrow operating range. The propulsive power of the kite system is entirely dependent on the wind conditions (speed and direction) and vessel velocity.

Furthermore, the system efficiency of a non-powered kite system drops as vessel velocity increases, and therefore the non-powered kite system technology only makes sense for slow vessels and/or windy routes. Moreover, only wind-powered operation is possible, thus limiting the technology to a power-assisting system, which could not take the place of marine propellers The present embodiments provide significant advantages over a flexible kite system. Using a rigid structure for the aerial wing compared to a flexible kite allows an order of magnitude higher performance (pulling power) per unit area of kite or aerial wing. In addition, using a powered aerial wing allows operation in the power generation mode and/or the powered flying mode as described above.

The powered flying mode advantageously increases the range of wind directions in which the system can be used. Furthermore due to the powered mode of operation, the system performance is less sensitive to vessel velocity compared to passive pulling only, i.e. such as provided by a non-powered flexible kite system. Moreover, because the present embodiments may operate over a wider range of wind directions, they could prove a cost-effective power-assist system for ships with power requirements ranging from kW's to MW's. In addition, they may also be useful to serve as a backup propulsion system in the event of an engine failure. When implemented, the present embodiments may lead to significant fuel savings and reduction in $CO_2$ emissions. In certain applications, because the present embodiments can be powered, they could actually replace the marine propeller(s) of a ship.

In addition, when the ship is docked, the airborne wind turbines may also be used to generate energy that may be used later for propulsion or other auxiliary purposes.

The present embodiments have been described with respect to use with a water-based vehicle such as a vessel or ship. However, the present embodiments may also be used in connection with pulling land-based vehicles such as trains, trucks, or buses, or even an aerial vehicle such as a balloon or blimp. For example, a blimp in the jetstream may harvest energy from surrounding air, or vice versa. Therefore as used herein the term "vehicle" includes water-based vehicles such as a vessel or ship, land-based vehicles such as a train, truck, or bus, as well as aerial vehicles such as a balloon or blimp.

2. Illustrative Vehicle-Based Airborne Wind Turbines

Figure 2:
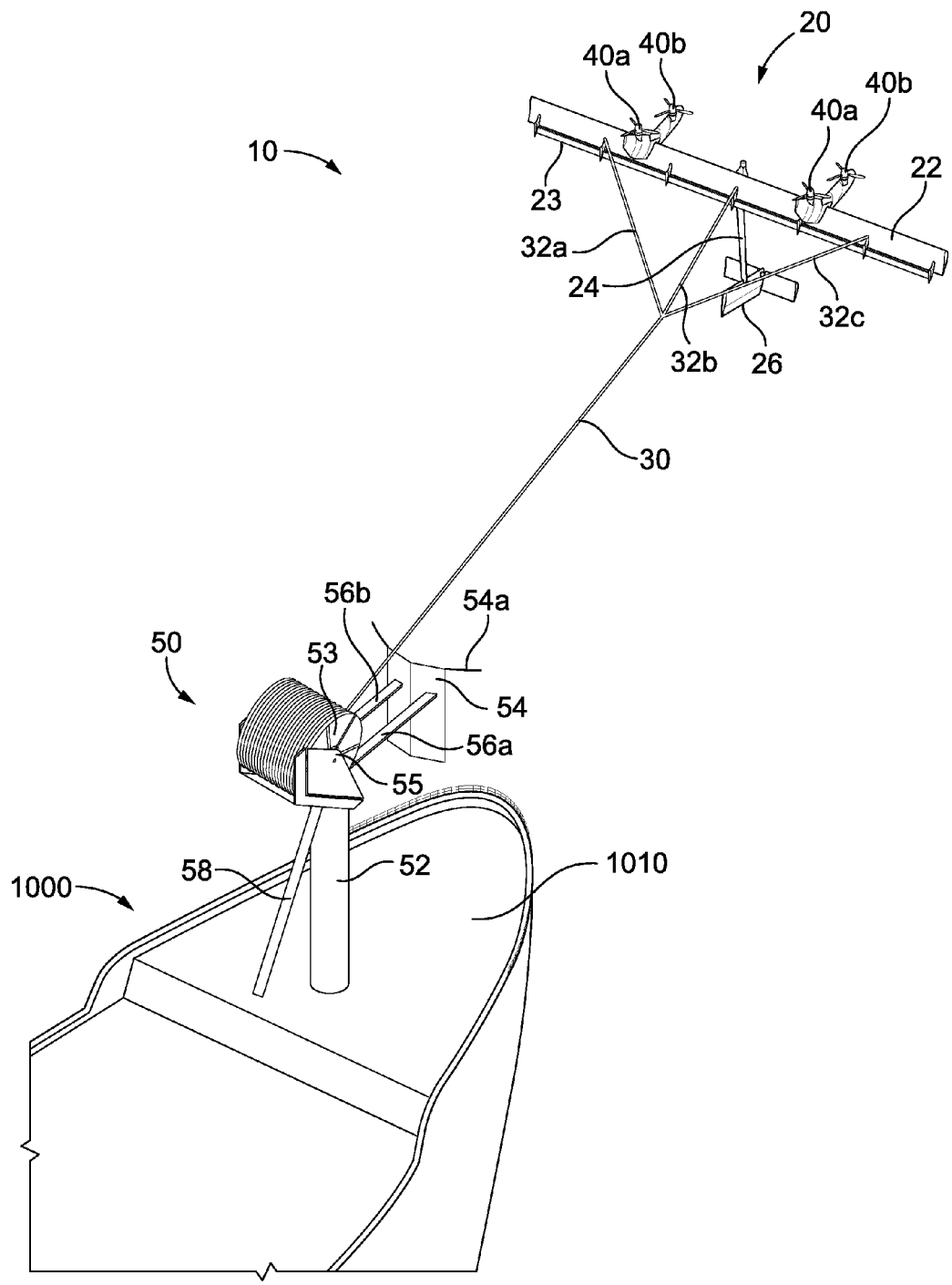
FIG. 2 is a close-up perspective view of the airborne wind turbine 10 and aerial vehicle 20 shown in FIG. 1.
Figure 3:
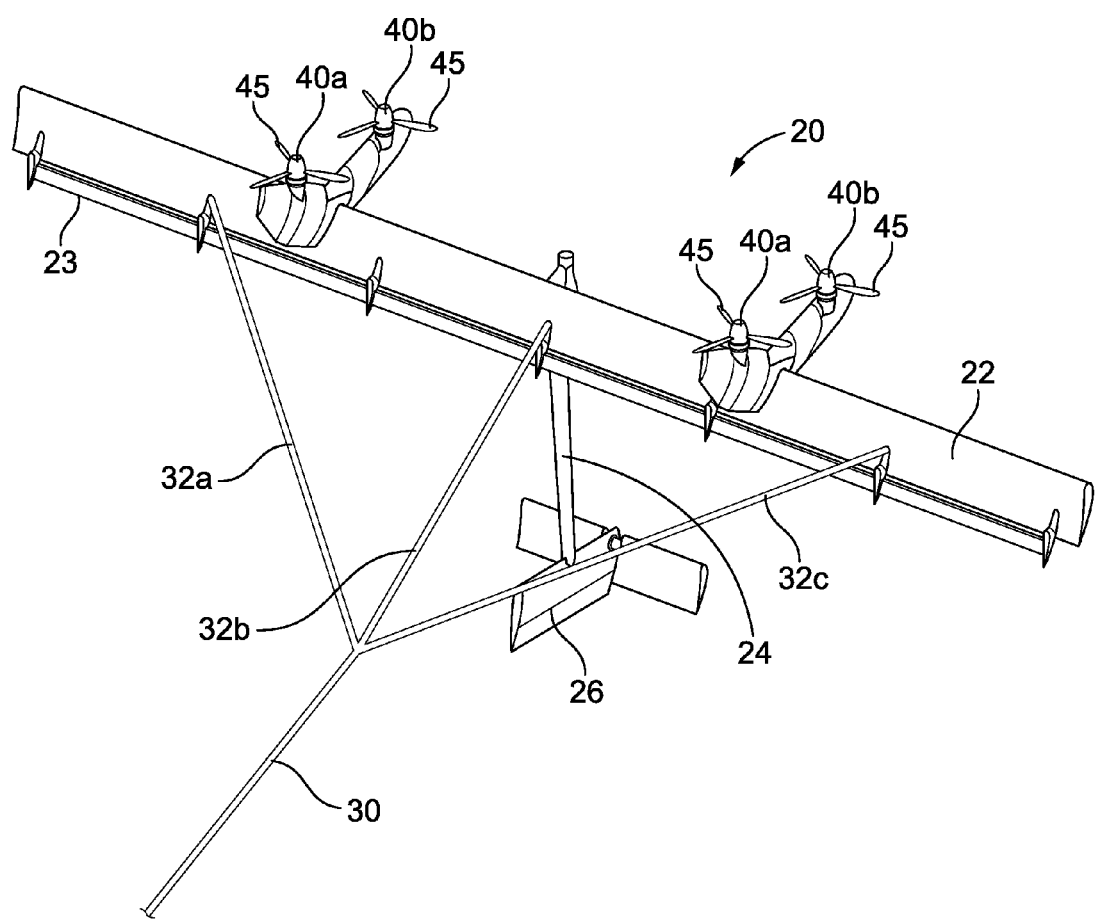
FIG. 3 is a close-up perspective view of the aerial vehicle 20 shown in FIGS. 1 and 2.

As disclosed in FIGS. 1-3, a vehicle-based airborne wind turbine system 10 is disclosed, according to an example embodiment. The airborne wind turbine system 10 is a wind based energy harnessing and energy generation device that includes an aerial vehicle 20 constructed of a rigid wing 22 with mounted turbines or rotors 40a, 40b that may fly in a path, such as a substantially circular path, across the wind. In an example embodiment, the aerial vehicle 20 may fly between 250 and 600 meters above the water to harness wind energy. However, an aerial vehicle may fly at other heights without departing from the scope of the invention.

In the flying mode of operation during cross wind flight, wind energy may be harnessed by the surface of the wing 22 that is facing the direction of the wind and a pulling force transmitted through the tether 30 to pull the ship.

Advantageously, electrical energy stored or generated on the ship 1000 can be delivered to the aerial wing 20 through the electrically conductive tether to operate the aerial wing in thrust generating mode while in the flying mode (powered flying mode). In some embodiments, the electrical energy may come from a generator installed on the main engine of a normal transport ship. In other embodiments, power for the aerial wing comes from an auxiliary engine of the ship, reducing required energy from the main engine, or comes from a water turbine used to generate electricity due to the boat's forward velocity in the water. In any event, in the powered flying mode, the energy may be used to power the blades 45 on the rotors 40a-40b on the aerial vehicle 20, such that the blades 45 serve to operate as thrust generating propellers, thereby providing a pulling force transferred through the tether 30 to the ship 1000.

As long as there is a component of the true wind speed in the travel direction of the vessel, the net propulsive efficiency using this powered flying mode mode is higher compared to a marine propeller referencing against water. Although electric energy is consumed in this mode, the propulsive efficiency is significantly higher than using a marine propeller. Under certain conditions, the net efficiency (electric power in/propulsive power out) can be on the order of 200%-300%. This can be achieved since the system is still extracting energy from the available wind field by harnessing energy in the same manner as in the flying mode, but also providing additional pulling force created by the power of the rotating blades 45 on the rotors 40a-40b. The powered flying mode of operation may be used on a boat where it is desired to be run at a constant speed to make port at a given time, as an example, or where speeds may be marginally increased or decreased according to wind availability.

In some embodiments, the power used to rotate the blades 45 of the rotors 40a-40b on the aerial wing may be delivered from the ship 1000 through the electrically conductive tether 30, and in other embodiments it may be from energy stored on the aerial vehicle 20.

In a third mode of operation, during the flying mode, the aerial vehicle may be operated in a power generation mode to convert kinetic wind energy to electrical energy. In the power generation mode of operation, the aerial vehicle 20 flies across the wind in a circular pattern similar to the tip of a wind turbine. The rotors 40a and 40b attached to the rigid wing 22 are used to generate power by slowing the wing 22 down. Air moving across the turbine blades forces them to rotate, driving a generator to produce electrical energy. The aerial vehicle 20 is connected to ship 1000 via an electrically conductive tether 30 that transmits power generated by the aerial vehicle 20 to the ship 1000 where it may be used for propulsive or auxiliary purposes. The energy generated during power generation mode may also be stored on the aerial wing and later used to power the rotors or other auxiliary purposes.

As shown in FIG. 1, the aerial vehicle 20 may be connected to the tether 30, and the tether 30 may be connected to a ground station 50. In this example, the tether 30 may be attached to the ground station at one location on the ground station 50, and attached to the aerial vehicle 20 at three locations on the aerial vehicle 20 using bridle 32a, 32b, and 32c. However, in other examples, the tether 30 may be attached at different locations on the ship 1000 or the aerial vehicle 20.

The ground station 50 may be used to hold and/or support the aerial vehicle 20 until it is in an operational mode. The ground station 50 may include a vertically oriented main member 52 that may extend above the deck 1010 of the ship 1000 on the order of 15 meters. However a main member is not required and the ground station could be located so that the end of the tether 30 extends into the hull of the ship to reduce the moment created when a main member 52 is extended above the deck 1010 of the ship 1000. The ground station 50 may also include a drum 53 rotatable about drum axis 55 that is used to reel in aerial vehicle 20 by winding the tether 30 onto the rotatable drum 53. In this example, the drum 53 is oriented horizontally, although the drum may also be oriented vertically (or at an angle). Further, the ground station 50 may be further configured to receive the aerial vehicle 20 during a landing. For example, perch support members 56a and 56b are attached to perch panel 54 and extend outwardly from rotatable drum 53. When the tether 30 is wound onto drum 53 and the aerial vehicle 20 is reeled in towards the ground station 50, the aerial vehicle 20 may come to rest upon perch panel 54.

During power generation mode, the tether 30 may transmit electrical energy generated by the aerial vehicle 20 to the ground station 50, which may then be used for propulsive or auxiliary purposes (e.g., stored). In addition, the tether 30 may transmit electricity to the aerial vehicle 20 in order to power the aerial vehicle 20 during takeoff, landing, hover mode, powered flying mode or other purposes, such as aileron control. The tether 30 may be constructed in any form and using any material which may allow for the transmission, delivery, and/or harnessing of electrical energy generated by the aerial vehicle 20 and/or transmission of electricity to the aerial vehicle 20. The tether 30 may also be configured to withstand one or more forces of the aerial vehicle 20 when the aerial vehicle 20 is in an operational mode. For example, the tether 30 may include a core configured to withstand one or more forces of the aerial vehicle 20 when the aerial vehicle 20 is in hover mode, flying mode, powered flying mode, or power generation mode. The core may be constructed of any high strength fibers or a carbon fiber rod. In some examples, the tether 30 may have a fixed length and/or a variable length. For example, in one example, the tether has a fixed length of 500 meters.

The aerial vehicle 20 may include or take the form of various types of devices, such as a kite, a helicopter, a wing and/or an airplane, among other possibilities. The aerial vehicle 20 may be formed of solid structures of metal, plastic and/or other polymers. The aerial vehicle 20 may be formed of any material which allows for a high thrust-to-weight ratio and generation of electrical energy which may be used in utility applications. Additionally, the materials may be chosen to allow for a lightning hardened, redundant and/or fault tolerant design which may be capable of handling large and/or sudden shifts in wind speed and wind direction. Other materials may be possible as well.

As shown in FIG. 1, and in greater detail in FIGS. 2 and 3, the aerial vehicle 20 may include a main wing 22, rotors 40a and 40b, tail boom or fuselage 24, and tail wing 26. Any of these components may be shaped in any form which allows for the use of components of lift to resist gravity and/or move the aerial vehicle 20 forward.

The main wing 22 may provide a primary lift for the aerial vehicle 20. The main wing 22 may be one or more rigid or flexible airfoils, and may include various control surfaces, such as winglets, flaps, rudders, elevators, etc. The control surfaces may be used to stabilize the aerial vehicle 20 and/or reduce drag on the aerial vehicle 20 during hover mode, flying mode, powered flying mode, and/or power generation mode. The main wing 22 may be any suitable material for the aerial vehicle 20 to engage in the operational modes and, for example, the main wing 20 may include carbon fiber and/or e-glass. Moreover, the main wing 22 may have a variety dimensions. For example, the main wing 22 may have one or more dimensions that correspond with a conventional wind turbine blade. As another example, the main wing 22 may have a span of 8 meters, an area of 4 meters squared, and an aspect ratio of 15.

Rotor connectors 43 may be used to connect the upper rotors 40a to the main wing 22, and rotor connectors 41 may be used to connect the lower rotors 40b to the main wing 22. In some examples, the rotor connectors 43 and 41 may take the form of or be similar in form to one or more pylons. In this example, the rotor connectors 43 and 41 are arranged such that the upper rotors 40b are positioned above the wing 22 and the lower rotors 40a are positioned below the wing 22.

The rotors 40a and 40b may be configured to drive one or more generators for the purpose of generating electrical energy, such as in power generation mode. In this example, the rotors 40a and 40b may each include one or more blades 45, such as three blades. The one or more rotor blades 45 may rotate via interactions with the wind and which could be used to drive the one or more generators. In addition, the rotors 40a and 40b may also be configured to provide a thrust to the aerial vehicle 20 during powered flying mode. With this arrangement, the rotors 40a and 40b may function as one or more propulsion units, such as a propeller. Although the rotors 40a and 40b are depicted as four rotors in this example, in other examples the aerial vehicle 20 may include any number of rotors, such as less than four rotors or more than four rotors, e.g. six or eight rotors.

Referring back to FIG. 1, when it is desired to land the aerial vehicle 20, the drum 53 is rotated to reel in the aerial vehicle 20 towards the perch panel 54 on the ground station 50, and the electrically conductive tether 30 is wound onto drum 53. Prior to landing on the perch panel 54, the aerial vehicle 20 transitions from a flying mode to a hover mode. The drum 53 is further rotated to further wind the tether 30 onto the drum 53 until the aerial vehicle 20 comes to rest on the perch panel 54.

3. Illustrative Examples of a Vehicle-Based Airborne Wind Turbine System

Figure 4:
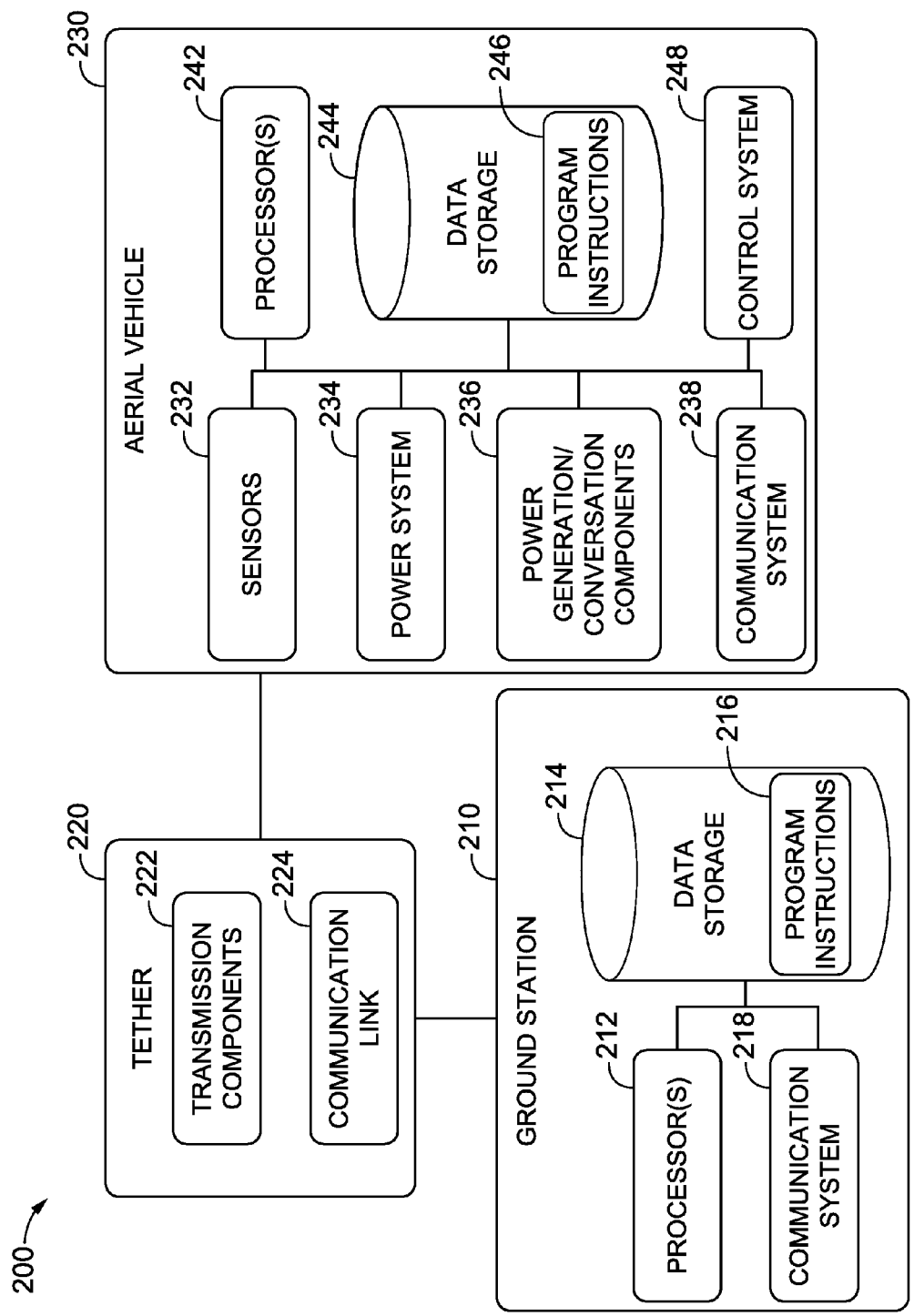
FIG. 4 is a simplified block diagram illustrating components of an airborne wind turbine, according to an example embodiment.

FIG. 4 is a simplified block diagram illustrating components of the AWT 200, which may take the form of AWT shown in FIG. 3. In particular, the AWT 200 includes a ground station 210, a tether 220, and an aerial vehicle 230, which may take the form of aerial vehicle 20 in FIGS. 1-3, or aerial vehicle 120 shown in FIGS. 5 and 6. The ground station 210 may take the form of or be similar in form to the ground station 50, the tether 220 may take the form of or be similar in form to the tether 30, and the aerial vehicle 230 may take the form of or be similar in form to the aerial vehicle 20 shown in FIGS. 1-3, or aerial vehicle 120 shown in FIGS. 5 and 6.

As shown in FIG. 4, the ground station 210 may include one or more processors 212, data storage 214, and program instructions 216. A processor 212 may be a general-purpose processor or a special purpose processor (e.g., digital signal processors, application specific integrated circuits, etc.). The one or more processors 212 can be configured to execute computer-readable program instructions 216 that are stored in a data storage 214 and are executable to provide at least part of the functionality described herein.

The data storage 214 may include or take the form of one or more computer-readable storage media that may be read or accessed by at least one processor 212. The one or more computer-readable storage media may include volatile and/or non-volatile storage components, such as optical, magnetic, organic or other memory or disc storage, which may be integrated in whole or in part with at least one of the one or more processors 212. In some embodiments, the data storage 214 may be implemented using a single physical device (e.g., one optical, magnetic, organic or other memory or disc storage unit), while in other embodiments, the data storage 214 can be implemented using two or more physical devices.

As noted, the data storage 214 may include computer-readable program instructions 216 and perhaps additional data, such as diagnostic data of the ground station 210. As such, the data storage 214 may include program instructions to perform or facilitate some or all of the functionality described herein.

In a further respect, the ground station 210 may include a communication system 218. The communications system 218 may include one or more wireless interfaces and/or one or more wireline interfaces, which allow the ground station 210 to communicate via one or more networks. Such wireless interfaces may provide for communication under one or more wireless communication protocols, such as Bluetooth, WiFi (e.g., an IEEE 802.11 protocol), Long-Term Evolution (LTE), WiMAX (e.g., an IEEE 802.16 standard), a radio-frequency ID (RFID) protocol, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. The ground station 210 may communicate with the aerial vehicle 230, other ground stations, and/or other entities (e.g., a command center) via the communication system 218.

In an example embodiment, the ground station 210 may include communication systems 218 that may allow for both short-range communication and long-range communication. For example, ground station 210 may be configured for short-range communications using Bluetooth and may be configured for long-range communications under a CDMA protocol. In such an embodiment, the ground station 210 may be configured to function as a "hot spot"; or in other words, as a gateway or proxy between a remote support device (e.g., the tether 220, the aerial vehicle 230, and other ground stations) and one or more data networks, such as cellular network and/or the Internet. Configured as such, the ground station 210 may facilitate data communications that the remote support device would otherwise be unable to perform by itself.

For example, the ground station 210 may provide a WiFi connection to the remote device, and serve as a proxy or gateway to a cellular service provider's data network, which the ground station 210 might connect to under an LTE or a 3G protocol, for instance. The ground station 210 could also serve as a proxy or gateway to other ground stations or a command station, which the remote device might not be able to otherwise access.

Moreover, as shown in FIG. 2, the tether 220 may include transmission components 222 and a communication link 224. The transmission components 222 may be configured to transmit electrical energy from the aerial vehicle 230 to the ground station 210 and/or transmit electrical energy from the ground station 210 to the aerial vehicle 230. The transmission components 222 may take various different forms in various different embodiments. For example, the transmission components 222 may include one or more conductors that are configured to transmit electricity. And in at least one such example, the one or more conductors may include aluminum and/or any other material that may allow for the conduction of electric current. Moreover, in some implementations, the transmission components 222 may surround a core of the tether 220 (not shown).

The ground station 210 may communicate with the aerial vehicle 230 via the communication link 224. The communication link 224 may be bidirectional and may include one or more wired and/or wireless interfaces. Also, there could be one or more routers, switches, and/or other devices or networks making up at least a part of the communication link 224.

Further, as shown in FIG. 2, the aerial vehicle 230 may include one or more sensors 232, a power system 234, power generation/conversion components 236, a communication system 238, one or more processors 242, data storage 244, and program instructions 246, and a control system 248.

The sensors 232 could include various different sensors in various different embodiments. For example, the sensors 232 may include a global a global positioning system (GPS) receiver. The GPS receiver may be configured to provide data that is typical of well-known GPS systems (which may be referred to as a global navigation satellite system (GNNS)), such as the GPS coordinates of the aerial vehicle 230. Such GPS data may be utilized by the AWT 200 to provide various functions described herein.

As another example, the sensors 232 may include one or more wind sensors, such as one or more pitot tubes. The one or more wind sensors may be configured to detect apparent and/or relative wind. Such wind data may be utilized by the AWT 200 to provide various functions described herein.

Still as another example, the sensors 232 may include an inertial measurement unit (IMU). The IMU may include both an accelerometer and a gyroscope, which may be used together to determine the orientation of the aerial vehicle 230. In particular, the accelerometer can measure the orientation of the aerial vehicle 230 with respect to earth, while the gyroscope measures the rate of rotation around an axis, such as a centerline of the aerial vehicle 230. IMUs are commercially available in low-cost, low-power packages. For instance, the IMU may take the form of or include a miniaturized MicroElectroMechanical System (MEMS) or a NanoElectroMechanical System (NEMS). Other types of IMUs may also be utilized. The IMU may include other sensors, in addition to accelerometers and gyroscopes, which may help to better determine position. Two examples of such sensors are magnetometers and pressure sensors. Other examples are also possible.

While an accelerometer and gyroscope may be effective at determining the orientation of the aerial vehicle 230, slight errors in measurement may compound over time and result in a more significant error. However, an example aerial vehicle 230 may be able mitigate or reduce such errors by using a magnetometer to measure direction. One example of a magnetometer is a low-power, digital 3-axis magnetometer, which may be used to realize an orientation independent electronic compass for accurate heading information. However, other types of magnetometers may be utilized as well.

The aerial vehicle 230 may also include a pressure sensor or barometer, which can be used to determine the altitude of the aerial vehicle 230. Alternatively, other sensors, such as sonic altimeters or radar altimeters, can be used to provide an indication of altitude, which may help to improve the accuracy of and/or prevent drift of the IMU.

As noted, the aerial vehicle 230 may include the power system 234. The power system 234 could take various different forms in various different embodiments. For example, the power system 234 may include one or more batteries for providing power to the aerial vehicle 230. In some implementations, the one or more batteries may be rechargeable and each battery may be recharged via a wired connection between the battery and a power supply and/or via a wireless charging system, such as an inductive charging system that applies an external time-varying magnetic field to an internal battery and/or charging system that uses energy collected from one or more solar panels.

As another example, the power system 234 may include one or more motors or engines for providing power to the aerial vehicle 230. In some implementations, the one or more motors or engines may be powered by a fuel, such as a hydrocarbon-based fuel. And in such implementations, the fuel could be stored on the aerial vehicle 230 and delivered to the one or more motors or engines via one or more fluid conduits, such as piping. In some implementations, the power system 234 may be implemented in whole or in part on the ground station 210.

As noted, the aerial vehicle 230 may include the power generation/conversion components 236. The power generation/conversion components 236 could take various different forms in various different embodiments. For example, the power generation/conversion components 236 may include one or more generators, such as high-speed, direct-drive generators. With this arrangement, the one or more generators may be driven by one or more rotors, such as the rotors 40a and 40b. And in at least one such example, the one or more generators may operate at full-rated-power wind speeds of 11.5 meters per second, at a capacity factor which may exceed 60 percent. As such, the one or more generators may generate electrical power from 40 kilowatts to 600 megawatts.

Moreover, as noted, the aerial vehicle 230 may include a communication system 238. The communication system 238 may take the form of or be similar in form to the communication system 218. The aerial vehicle 230 may communicate with the ground station 210, other aerial vehicles, and/or other entities (e.g., a command center) via the communication system 238.

In some implementations, the aerial vehicle 230 may be configured to function as a "hot spot"; or in other words, as a gateway or proxy between a remote support device (e.g., the ground station 210, the tether 220, other aerial vehicles) and one or more data networks, such as cellular network and/or the Internet. Configured as such, the aerial vehicle 230 may facilitate data communications that the remote support device would otherwise be unable to perform by itself.

For example, the aerial vehicle 230 may provide a WiFi connection to the remote device, and serve as a proxy or gateway to a cellular service provider's data network, which the aerial vehicle 230 might connect to under an LTE or a 3G protocol, for instance. The aerial vehicle 230 could also serve as a proxy or gateway to other aerial vehicles or a command station, which the remote device might not be able to otherwise access.

As noted, the aerial vehicle 230 may include the one or more processors 242, the program instructions 244, and the data storage 246. The one or more processors 242 can be configured to execute computer-readable program instructions 246 that are stored in the data storage 244 and are executable to provide at least part of the functionality described herein. The one or more processors 242 may take the form of or be similar in form to the one or more processors 212, the data storage 244 may take the form of or be similar in form to the data storage 214, and the program instructions 246 may take the form of or be similar in form to the program instructions 216.

Moreover, as noted, the aerial vehicle 230 may include the control system 248. In some implementations, the control system 248 may be configured to perform one or more functions described herein. The control system 248 may be implemented with mechanical systems and/or with hardware, firmware, and/or software. As one example, the control system 248 may take the form of program instructions stored on a non-transitory computer readable medium and a processor that executes the instructions. The control system 248 may be implemented in whole or in part on the aerial vehicle 230 and/or at least one entity remotely located from the aerial vehicle 230, such as the ground station 210. Generally, the manner in which the control system 248 is implemented may vary, depending upon the particular application.

While the aerial vehicle 230 has been described above, it should be understood that the methods and systems described herein could involve any suitable aerial vehicle that is connected to a tether, such as the tether 230 and/or the tether 30.

Figure 5:
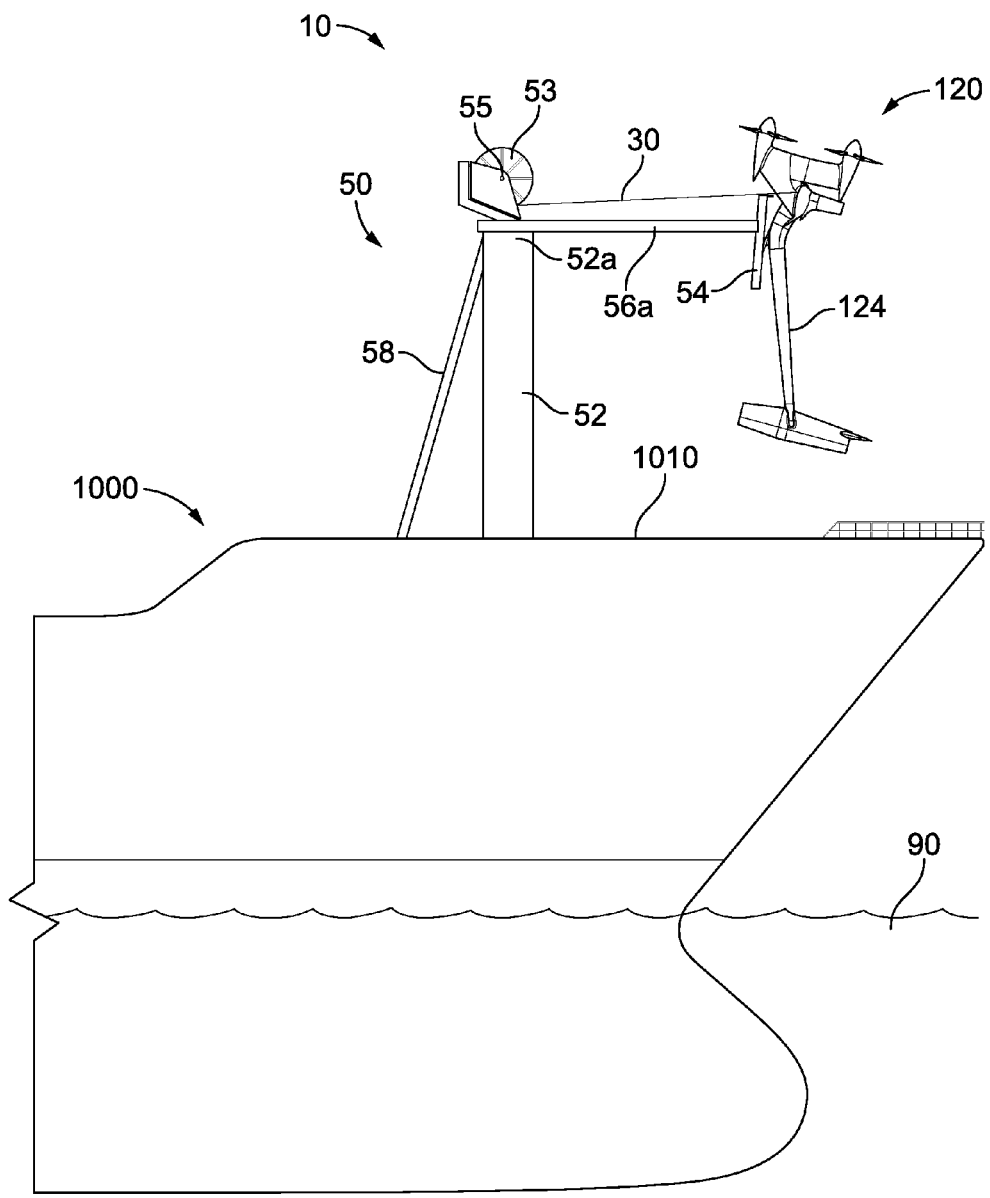
FIG. 5 is a side view of airborne wind turbine 10 with an aerial vehicle 120 positioned on a perch 54, with an electrically conductive tether 30 attaching the ship 1000 to aerial vehicle 120, according to an example embodiment.
Figure 6:
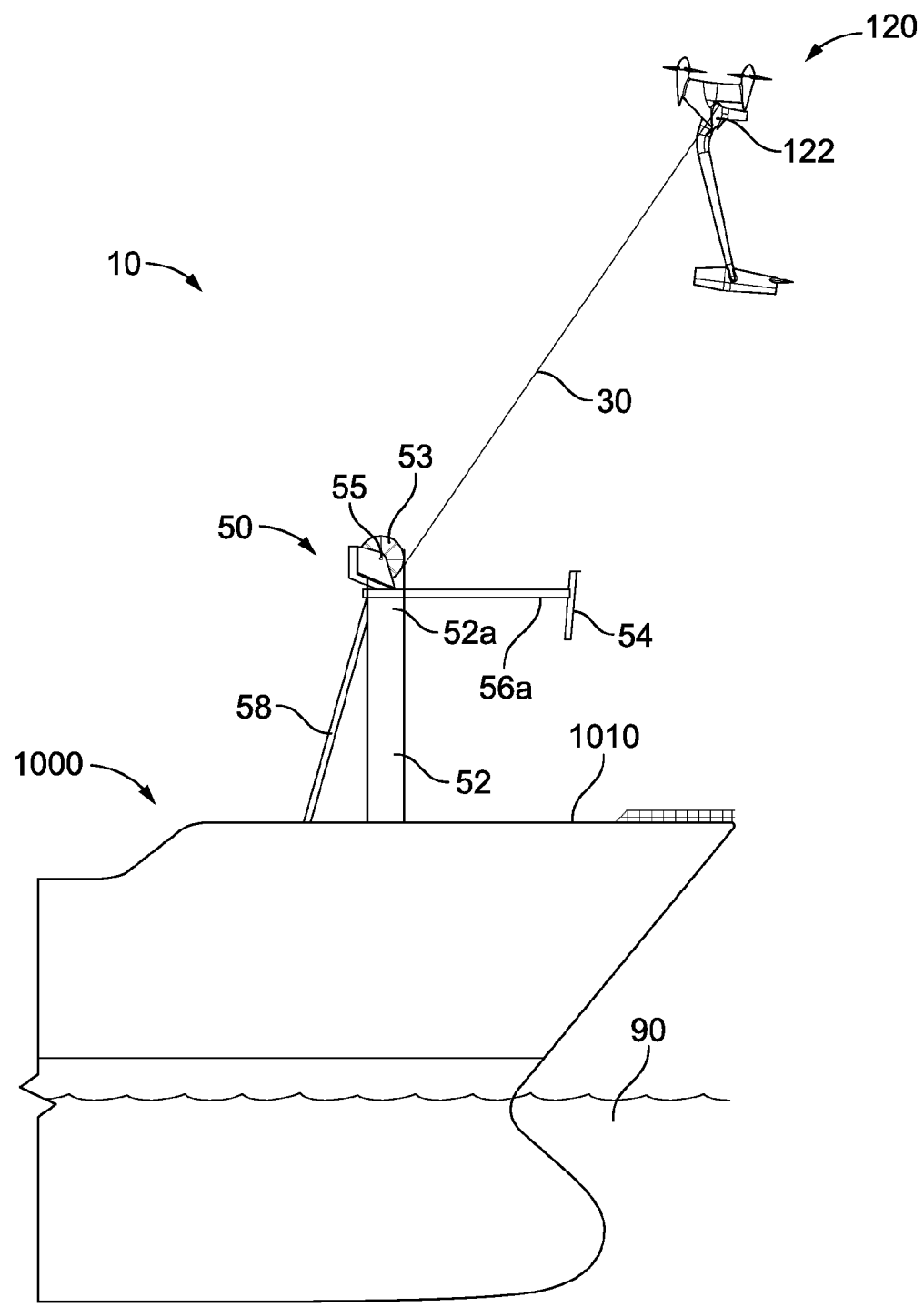
FIG. 6 is a side view of airborne wind turbine 10 shown in FIG. 5, with the aerial vehicle 120 unreeling from rotatable drum 53 positioned on ship 1000, according to an example embodiment.

FIGS. 5 and 6 show an example embodiment of vehicle-based airborne wind turbine 10 that includes aerial vehicle 120 having a fuselage 124. In FIG. 5, aerial vehicle 120 is shown perched on perch panel 54 extending from perch support 56a attached to ground station 50. An electrically conductive tether 30 is shown extending from rotatable drum 53 that rotates about horizontal drum axis 55 to aerial vehicle 120. The rotatable drum 53 is positioned atop upper end 52a of main vertical member 52. An extending arm 58 extends from the top 52a of main member 52 to provide additional truss support to the main member 52.

FIG. 6 is a side view of the airborne wind turbine 10 shown in FIG. 5, with the aerial vehicle 120 unreeling from rotatable drum 53. Rotatable drum 53 may be used to store the tether 30 as it is reeled in towards the ground station 50 during a landing procedure. In a one embodiment, the drum 53 may rotate about horizontal axis 55.

FIG. 7A is a top view of the perch platform 95 that may be used, with tether 30 extending from rotatable drum 53 with perch platform 95 attached to perch supports 56a and 56b attached to perch panel 54 and perch bar 54a in a first position relative to extending arm 58, according to an example embodiment.

FIG. 7B is a top view of the perch platform 95 shown in FIG. 7A with tether 30 extending from rotatable drum 53 with perch platform 95 attached to perch supports 56a and 56b attached to perch panel 54 and perch bar 54a in a second position relative to extending arm 58, according to an example embodiment.

FIG. 7C is a top view of the perch platform 50 shown in FIGS. 7A-7B with tether 30 extending from rotatable drum 53 with perch platform 95 attached to perch support 56a and 56b attached to perch panel 54 and perch bar 54a in a third position relative to extending arm 58, according to an example embodiment.

In the embodiments shown in FIGS. 7A-7C, perch platform 95, perch supports 56a and 56b and perch panel 54 may rotate about the top 52a of main element 52 to allow for a desired positioning of the perch panel 54 during landing and launch.

It will be appreciated that the tether 30 must withstand significant tension forces. For example, the tension of the tether during crosswind flight may be 15 kilonewtons (KN), and even great during powered flying mode. Tether 30 may be constructed of a carbon fiber core surrounded by aluminum conductors. The carbon fiber core and aluminum conductors may be positioned within an outer insulation. In an example embodiment that may be used in the present embodiments, the diameter of the carbon fiber core is 14 millimeters and the diameter of the tether is 24 millimeters.

The positioning of the rotatable drum 53 and/or rotation of the perch platform 95 may be used for purposes of steering or turning the ship 1000. For example, the aerial wing 120 could fly in a direction perpendicular to the longitudinal axis of the ship 1000, and when attached at the front of the ship (as shown in FIGS. 1 and 2) would tend to turn or steer the ship to the right (or left). This ability to use forces from the aerial wing 120 to turn or steer the ship may be advantageous. In particular, if a tight turning radius is required or if the rudder or steering mechanism onboard the ship is not working properly, then the aerial vehicle could be used to turn or steer the ship. Furthermore, if there was a need to turn the ship quickly, the aerial vehicle could be used to turn the ship more quickly and with a smaller turning radius than using only the marine propeller propulsion system on the ship. In some embodiments the aerial wing could fly in direction having a component vector opposite of the movement of the ship, and even against the wind, to perform the steering or turning functions. For example, the aerial wing may fly between at an angle of 45 and 135 degrees from the longitudinal axis or the ship to effect a steering or turning maneuver in certain applications.

In some applications, it may be possible to include two or more aerial vehicles to provide more pulling force than a single aerial vehicle.

4. Illustrative Ocean-Going Vessels

Figure 8A:
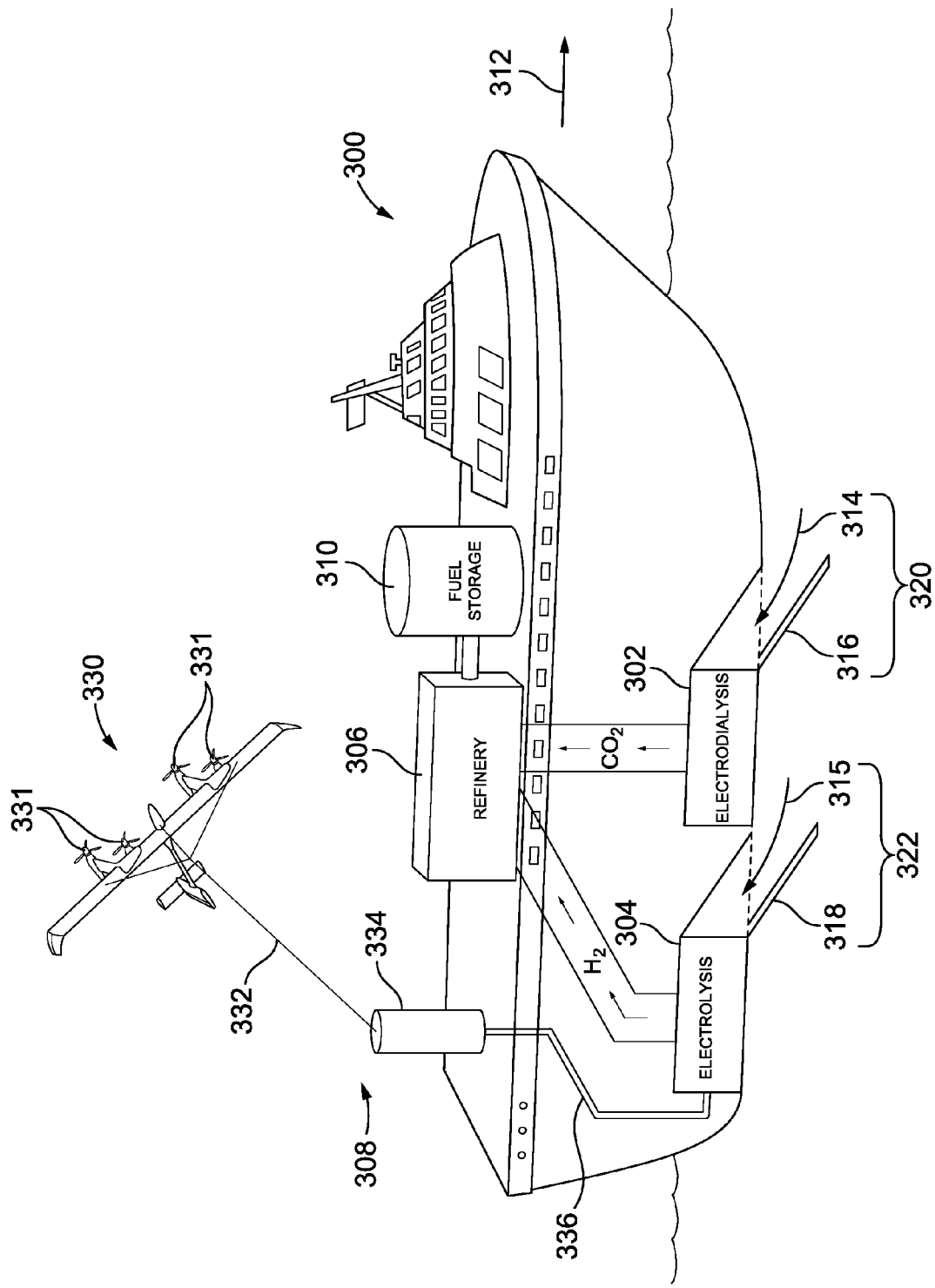
FIG. 8A is a simplified illustration of an ocean-going vessel 300, according to an example embodiment.

FIG. 8A is a simplified illustration of an ocean-going vessel 300, according to an example embodiment. As shown, the ocean-going vessel 300 includes an electrodialysis system 302, an electrolysis system 304, a refinery system 306, an AWT 308, and a fuel storage container 310.

In the illustrated example, the ocean-going vessel 300 is a ship. As such, ocean-going vessel 300 may include one or more electric- or gas-powered propulsion systems (e.g., engines coupled to submerged propellers) that are typical of ships. Other types of propulsion systems are also possible. Alternatively, ocean-going vessel 300 could be a sailboat. Further, ocean-going vessel 300 may be implemented on various types of ships, which may have various types of hulls, and which may have a different number of hulls (e.g., a single-hull, a catamaran, a trimaran, etc.).

Figure 10:
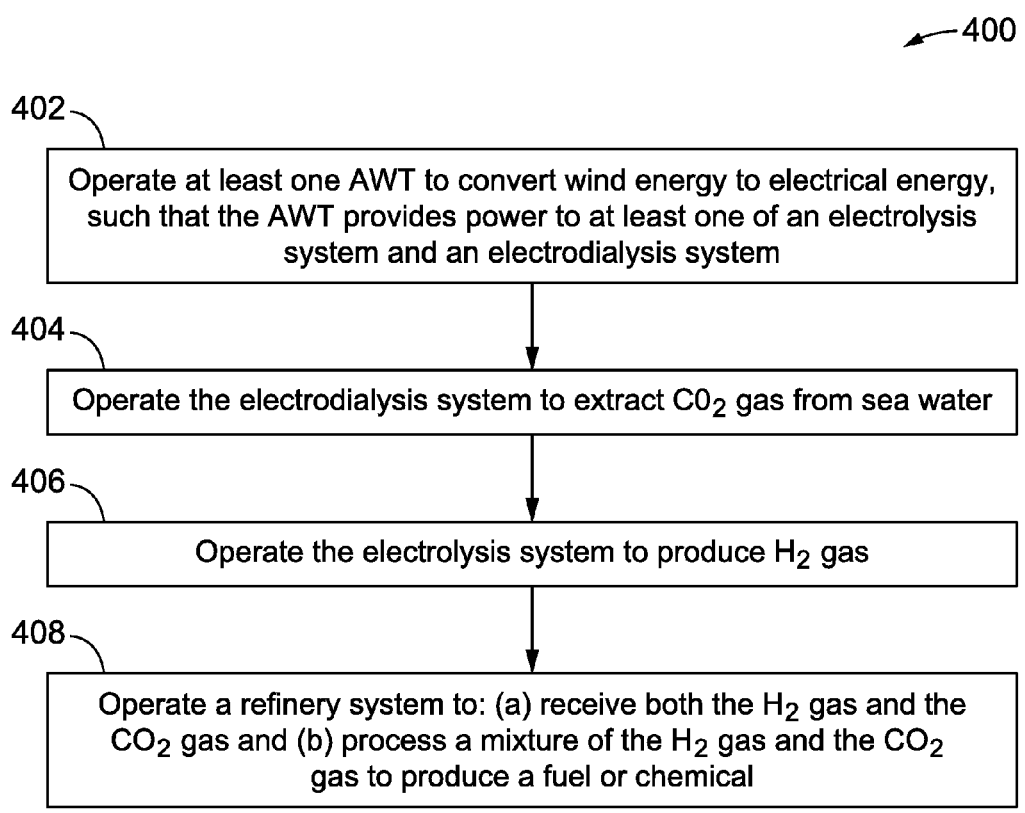
FIG. 10 is a flowchart illustrating a process that may be implemented by one or more control systems on an ocean-going vessel, according to an example embodiment.

FIG. 10 is a flow chart illustrating a process that may be implemented by one or more control systems on an ocean-going vessel that includes an AWT, according to an example embodiment. As shown, method 400 involves operating at least one AWT to convert wind energy to electrical energy, such that the AWT provides power to at least one of an electrolysis system and an electrodialysis system for at least some period of time, where both the electrodialysis system and the electrolysis system are disposed on an ocean-going vessel, as shown by block 402. Further, method 400 involves operating the electrodialysis system to extract carbon dioxide ($CO_2$) gas from seawater, and operating the electrolysis system to apply electrolysis to seawater to produce hydrogen ($H_2$) gas, as shown by blocks 404 and 406, respectively. Yet further, method 400 involves operating a refinery system to: (a) receive both the $H_2$ gas produced by electrolysis system and the $CO_2$ gas extracted by the electrodialysis system and (b) process a mixture of the $H_2$ gas and the $CO_2$ gas to produce a fuel or chemical, as shown by block 408.

A. Electrodialysis Systems

Referring again to FIG. 8A, in an example embodiment, ocean-going vessel 300 includes an electrodialysis system 302, which is configured to extract carbon dioxide ($CO_2$) from seawater that passes through one or more membranes of the electrodialysis system 302. The $CO_2$ that is produced can then be supplied to the refinery system 306.

Further, once a BPMED system removes the dissolved $CO_2$ from the acidified seawater, the acidified seawater can be combined with the basified seawater. Combining the stripped and acidified seawater with the basified seawater may neutralize the pH of the resulting solution, such that it can be safely output into the ocean.

In some embodiments, an ocean-going vessel 300 may include a system that uses fractional distillation of water to separate $CO_2$ from other absorbed gases. Other techniques for extracting $CO_2$ from seawater are also possible. In general, it is contemplated that an ocean-going vessel 300 may use any feasible technique and/or system for extracting $CO_2$ from seawater In a further aspect, an intake 320 is arranged such that movement of the vessel through water forces seawater to flow into the electrodialysis system 302. In the illustrated configuration, the intake 320 includes an angled feature 316. The angled feature extends from the bottom of the vessel 300, such that when the vessel moves through water (e.g., in the general direction indicated by arrow 312), water is forced to flow through the intake 320 into electrodialysis system 302, as indicated by arrow 314. This intake configuration may be beneficial as it uses the motion of the vessel through the water to provide the energy needed to move seawater to the electrodialysis system 302, and thus may alleviate the need to use an electric or fuel-powered pump to supply seawater to and/or move seawater through the electrodialysis system 302.

It should be understood that intake 320 is just one example of a structural design that forces water into the electrodialysis system 302, and thus alleviates or reduces the need for a pump. It is contemplated that other structural designs providing similar functionality may be utilized. Further, it is possible that an ocean-going vessel may utilize one or more pumps to supply seawater to and/or move seawater through the electrodialysis system 302, instead of or in addition to using a structural design that forces water to the electrodialysis system 302.

As one additional example, in some embodiments, the intake to the electrodialysis system 302 and/or to the electrolysis system 304 may include an impeller through which water flows before entering the electrodialysis system 302 and/or to the electrolysis system 304. As such, when the vessel moves forward the forward motion of the vessel creates a pressure gradient that pulls water through the intake and spins the impeller, thus increasing the pressure of water flowing into the electrodialysis system 302 and/or into the electrolysis system 304.

B. Electrolysis Systems

In an example embodiment, ocean-going vessel 300 includes an electrolysis system 304, which is configured to apply electrolysis to seawater to produce hydrogen ($H_2$). In particular, the electrolysis system 304 takes in and processes seawater in order to produce $CO_2$ $H_2$ gas; e.g., by applying a current to water to drive the following reaction: $2 H_2O \rightarrow 2 H_2 + O_2$.

The $H_2$ gas that is produced by electrolysis system 304 can then be supplied to the refinery system 306 for production of fuels or chemicals. Further, the oxygen ($O_2$) gas that is produced by the electrolysis system 304 may be vented into the atmosphere or used for some other purpose.

In a further aspect, an intake 322 is arranged such that movement of the vessel through water forces seawater to flow into the electrolysis system 304. In the illustrated configuration, the intake 322 includes an angled feature 318, which functions similarly to the angled feature 316 of intake 320. As such, when the vessel moves through water (e.g., in the general direction indicated by arrow 312), water is forced to flow through intake 322 into electrolysis system 304, as indicated by arrow 315.

It should be understood that intake 322 is just one example of a structural design that forces water into the electrolysis system 304 and thus alleviates the need for a pump to do so. It is contemplated that other structural designs providing similar functionality may be utilized. Further, it is possible that an ocean-going vessel may utilize one or more pumps to supply seawater to and/or move seawater through the electrolysis system 304, instead of or in addition to using a structural design that forces water to the electrolysis system 304.

C. Illustrative Airborne Wind Turbines

As noted above, ocean-going vessel 300 includes an AWT 308, which is operable generate electrical energy for the vessel. As such, the AWT 308 may be utilized to generate power for the electrolysis system 304, the electrodialysis system 302, and/or other components or systems on the ocean-going vessel 300. The AWT 308 may take a form and operate as described in reference to FIGS. 1-3, 5, 6, and 7A-7B, or may take another form and/or may operate in a different manner.

As described above, an AWT such as AWT 308 may be configured to operate in a hover-flight mode, as well as in a flying mode or powered flying mode. In a further aspect of some embodiments, an AWT 308 may be configured to operate in a vessel-steering mode. In such an embodiment, the AWT 308 may fly so as to steer and/or pull the ocean-going vessel 300.

Figure 8B:
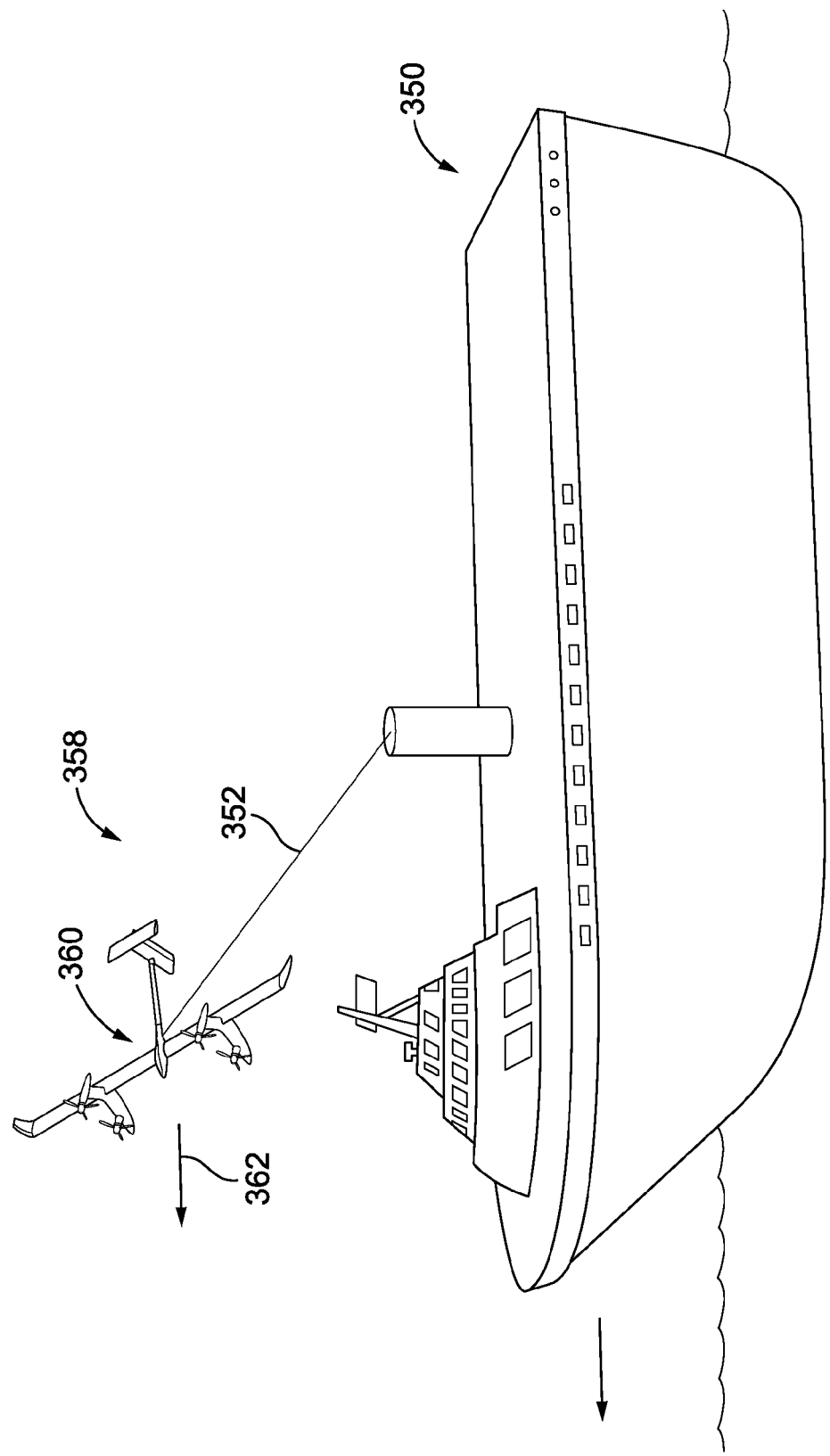
FIG. 8B is an illustration showing an airborne wind turbine installed on an ocean-going vessel 300 and operating in a vessel-steering mode, according to an example embodiment.

For example, FIG. 8B is an illustration showing an AWT 358 operating in a vessel-steering mode. As shown, in the vessel steering mode, the aerial vehicle 360 may be positioned for forward flight in the direction indicated by arrow 362. (Note that "forward flight" should be understood to mean that at least a component of the vehicle's trajectory is in the forward direction.) Thus, the aerial vehicle may use its propulsion system (e.g., its rotors, which also function as wind turbines when in power generation mode) to create a thrust vector having a horizontal component as indicated by arrow 362, such that it tows the ocean-going vessel 350 via tether 352.

In some embodiments, the aerial vehicle 360 may be configured to tow the ocean-going vessel 350 in a desired direction. To do so, the aerial vehicle 360 may maneuver such that its thrust vector has a horizontal component in the direction in which it is desired for the vessel to travel. Doing so may cause the vessel 350 to turn until the vessel's is travelling in the direction of the horizontal component of the aerial vehicle's thrust vector.

In a further aspect, an aerial vehicle may be operable to tow the vessel 350 in order to assist the vessel in turning. For example, if the ocean-going vessel 350 is using its own propulsion and steering systems to turn to the right or the left, the aerial vehicle may operate in forward-flight mode and turn right or left such that the horizontal component of its thrust vector is angled to the right or left of the vessel's current direction of travel. Doing so may thus help the ocean-going vessel 350 to turn more quickly than it otherwise could, if only using its other propulsion systems.

In some embodiments, the aerial vehicle 360 may be configured to tow the ocean-going vessel 350 in a desired direction, while at the same time operating in a power generation mode. For example, a route may be chosen which provides mostly down-wind travel for high efficiency. In particular, while aerial vehicle 360 is in crosswind-flight, there may be a horizontal component of the force that the aerial vehicle 360 exerts on the vessel 350. The vessel 350 may further include a keel and/or a rudder (or other features), that can help to steer the vessel when the horizontal component of the force that the aerial vehicle 360 exerts on the vessel differs from the desired direction of travel. Essentially, the aerial vehicle may operate in a similar manner as a traditional sail does, in conjunction with a keel and/or a rudder (or other features), in order to steer vessel 350.

D. Illustrative Power Systems

Referring back to FIG. 8A, in an exemplary embodiment, some or all of the energy that used to power the electrolysis system 304 may be provided by the AWT 308. Accordingly, the ground station of the AWT may be electrically connected to the electrolysis system, such that electrical power that is generated by airflow rotating the rotors of the aerial vehicle 330 can be relayed to the electrolysis system 304 via the tether 332, ground station 334, and an electrical connection 336. Provided with this electricity source, the electrolysis system 304 can then apply a current to water to perform electrolysis. Further, note that while electrical connections between the AWT 308 and other components of the ocean-going vessel are not shown in FIG. 8A, the AWT 308 may also be electrically coupled to other components, such as electrodialysis system 302, in order to provide generated electrical power to such components.

In some embodiments, other energy sources may be used to supplement the power provided by AWT 308. For example, ocean-going vessel 300 may utilize one or more other renewable or "green" energy sources, such as a solar energy generation system (e.g., solar cells), a bio-fuel energy generation system, and/or a synthetic fuel energy generation system, among other possibilities. An ocean-going vessel 300 could additionally or alternatively utilize a low carbon power generation method to supplement the AWT 308, such as by including a nuclear power system that generates electricity for the vessel. Further, in some embodiments, ocean-going vessel 300 could also utilize one or more non-renewable sources energy sources, such as by using an internal combustion engine and/or other types of energy generation systems that burn a fossil fuel. (Preferably, however, the ocean-going vessel 300 is designed so as to minimize and hopefully eliminate use of such fossil fuels.)

In some scenarios, the ocean-going vessel 300 may even be configured to power its systems using some of the fuel that has been stored fuel storage container 310, which was previously produced by its refinery system 306. For example, there might be scenario where there is an extended period of without winds that are suitable for electrical power generation by the AWT, and/or where conditions are such that other green energy sources are not able to generate adequate amounts of energy to power the ocean-going vessel 300. In such a scenario, the ocean-going vessel 300 might utilize some of the fuel that the refinery system 306 has produced and stored in fuel storage container 310 in order that the vessel can continue operation until winds are again conducive for electrical power generation by the AWT and/or until conditions are such that another green power generation system can again be utilized to power the vessel.

E. Illustrative Refinery Systems

In an example embodiment, ocean-going vessel 300 includes at least one refinery system 306. The refinery system 306 is operable to use both the $H_2$ produced by electrolysis system 304 and the $CO_2$ extracted by the electrodialysis system 306 to produce at least one type of fuel or petrochemical. Further, in some embodiments, an ocean-going vessel 300 may include multiple refinery systems, such that the vessel is capable of producing multiple types of fuels or petrochemicals. It is also possible that a single refinery system may be operable to produce a number of different types of fuels or petrochemicals. In embodiments, where an ocean-going vessel 300 is capable of producing two or more different types of fuels or petrochemicals, the vessel may include multiple storage containers 310, such that the each fuel or petrochemical can be stored in a separate container.

Various types of refinery systems, which produce various fuels or petrochemicals from the inputs of hydrogen ($H_2$) and carbon dioxide ($CO_2$), are currently known in the art. Further, there is much interest in developing new and more efficient processes for producing fuel from renewable inputs such as hydrogen ($H_2$) and carbon dioxide ($CO_2$) (and from $CO_2$ in particular, due to the urgent need to prevent further increase, and hopefully decrease, the amount of $CO_2$ in the atmosphere and oceans).

Some examples of processes that may be used by a refinery system 306 will now be described. In some embodiments, refinery system 306 may use a number of catalyzed syngas reactions to selectively produce ethanol directly from $CO_2$ and $H_2$. In some cases, $CO_2$ and $H_2$ may be used to create methanol, which may then be used to create ethanol. However, it should be understood that these examples are provided for explanatory purposes, and are not intended to be limited. It is contemplated that an ocean-going vessel's refinery system could potentially utilize any process that is currently known or later developed for fuel or chemical production using $H_2$ and $CO_2$ as inputs.

In some embodiments, a refinery system 306 may include or take the form of a Fischer-Tropsch reactor, which utilizes a Fischer-Tropsch process to produce a liquid hydrocarbon. A typical Fischer-Tropsch process involves a sequence of chemical reactions that produces a liquid hydrocarbon from a mixture of carbon monoxide (CO) and hydrogen ($H_2$) gases (a mixture that may also be referred to as "syngas"). For instance, a number of useful hydrocarbons following the formula of $C_nH_{(2n+2)}$ may be produced using Fischer-Tropsch processes. In particular, various Fischer-Tropsch processes may produce such hydrocarbons via reactions that follow the formula of: $(2n+1) H_2 + n\ CO \rightarrow C_nH_{(2n+2)} + n\ H_2O$.

Since a typical Fischer-Tropsch process utilizes carbon monoxide (CO) as an input, a refinery system 306 may be configured to produce CO from the $CO_2$ that is supplied by electrodialysis system 302. For example, refinery system 306 may implement a reverse water gas shift process that takes $H_2$ and $CO_2$ gases as inputs and produces carbon monoxide and water as follows: $11\ CO_2 + 11\ H_2 \rightarrow 11\ CO + 11\ H_2O$. Other examples are also possible. The carbon monoxide that is produced from such a process may then be used in a Fischer-Tropsch process. Further, the ocean-going vessel 300 may release the water that is produced in the reverse water gas shift process back into the ocean, and/or use this water for other purposes.

In an exemplary embodiment, a Fischer-Tropsch process may be used to produce a synthetic fuel (also referred to as a "synfuel") from syngas. The refinery system 306 may be further configured to process some or all of the synthetic fuel to convert the synthetic fuel into ethanol. For example, the refinery system 306 may use syngas fermentation, which is a microbial process where certain microorganisms, such as various acetogens, are used to produce ethanol and other chemicals via syngas utilization.

In some embodiments, a refinery system 306 could utilize a Fischer-Tropsch process to produce synthetic jet fuel (e.g., $C_{11}H_{24}$) or a synthetic diesel fuel, which may then be stored in an appropriately-designed fuel storage container 310. For example, $H_2$ and $CO_2$ may be used by the refinery as inputs to a reverse water gas shift process that produces carbon monoxide and water as described above. The following Fischer-Tropsch process may then be applied to convert a mixture of the carbon monoxide and hydrogen into a liquid jet fuel and oxygen gas as follows: $11\ CO_2 + 12\ H_2O \rightarrow C_{11}H_{24} + 17\ O_2$.

Other types of Fischer-Tropsch processes may be implemented by an example refinery system 306. Additionally or alternatively, a refinery system may implement processes other than Fischer-Tropsch processes, which utilize $H_2$ and $CO_2$ to produce ethanol and/or other fuels and/or chemicals.

5. Example Method of Pulling a Vehicle with an Aerial Wind Turbine System

Figure 9:
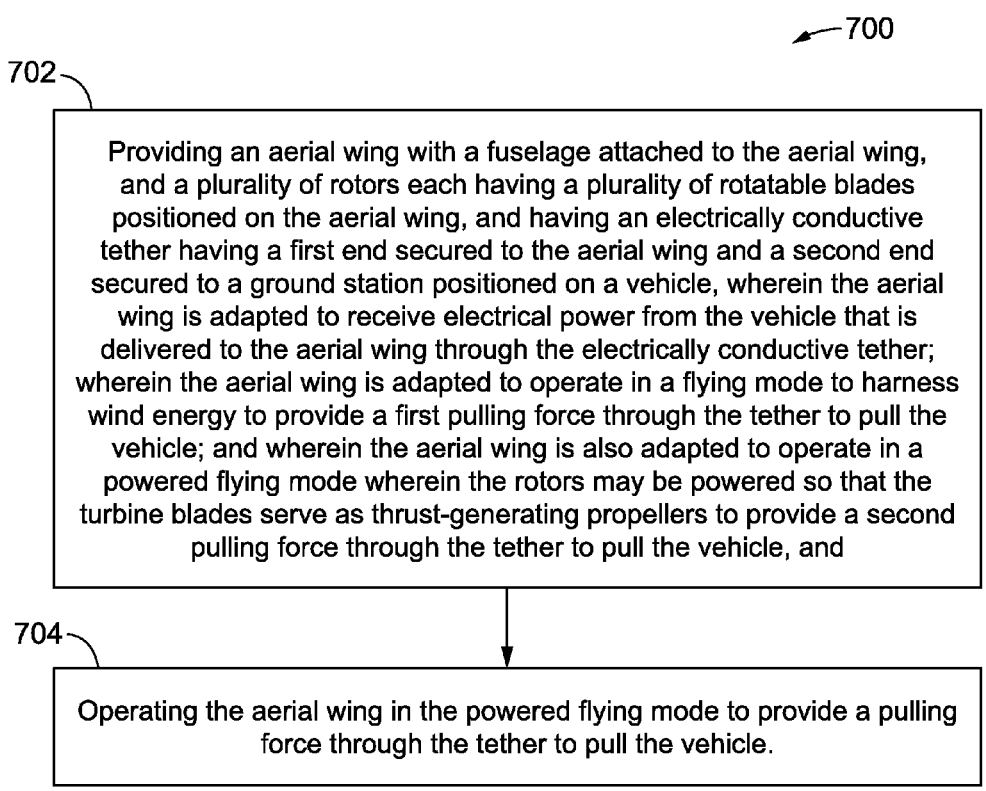
FIG. 9 is a method of pulling a vehicle, according to an example embodiment.

FIG. 9 shows a method 700 that may be used for pulling a vehicle with an aerial wind turbine system. Method 700 includes the step 702 of providing an aerial wing with a fuselage attached to the aerial wing, and a plurality of rotors each having a plurality of rotatable blades positioned on the aerial wing, and having an electrically conductive tether having a first end secured to the aerial wing and a second end secured to a ground station positioned on a vehicle, wherein the aerial wing is adapted to receive electrical power from the vehicle that is delivered to the aerial wing through the electrically conductive tether; wherein the aerial wing is adapted to operate in a flying mode to harness wind energy to provide a first pulling force through the tether to pull the vehicle; and wherein the aerial wing is also adapted to operate in a powered flying mode wherein the rotors may be powered so that the turbine blades serve as thrust-generating propellers to provide a second pulling force through the tether to pull the vehicle, and the step 704 of operating the aerial wing in the powered flying mode to provide a pulling force through the tether to pull the vehicle.

Method 700 may further optionally include the step of including the step of operating the aerial wing in power generation mode during the powered flying mode where air moving across the rotatable blades of one or more of the rotors forces them to rotate, thereby driving a generator to produce electrical energy.

The present embodiments may be used to provide a pulling force to pull the ship by operating the aerial wing in flying mode or powered flying mode, while at the same time operating the aerial wing in power generation mode, wherein the generated power may be used to power an electrolysis system or an electrodialysis system located on board the ship. The electrodialysis system may then be used to extract carbon dioxide ($CO_2$) gas from seawater, and the electrolysis system may be used to apply electrolysis to seawater to produce hydrogen ($H_2$). A further process may be used to process a mixture of the $H_2$ gas and the $CO_2$ gas to produce a fuel or chemical.

5. Conclusion

The above detailed description describes various features and functions of the disclosed systems, devices, and methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A vehicle-based airborne wind turbine system, comprising:
    an aerial wing;
    a plurality of rotors each having a plurality of rotatable blades positioned on the aerial wing;
    an electrically conductive tether having a first end secured to the aerial wing and a second end secured to a ground station positioned on a vehicle;
    wherein the aerial wing is adapted to receive electrical power from the vehicle that is delivered to the aerial wing through the electrically conductive tether;
    wherein the aerial wing is adapted to (i) operate in a flying mode to harness wind energy to provide a first pulling force through the tether to pull the vehicle; and (ii) operate in a powered flying mode during cross-wind flight wherein the rotors may be powered so that the rotatable blades serve as thrust-generating propellers to provide a second pulling force through the tether to pull the vehicle, and
    wherein the ground station is attached to the vehicle such that the aerial wing is adapted to operate in the powered flying mode to steer or turn the vehicle.

2. The system of claim 1, wherein when the aerial wing is operated in the powered flying mode, the rotors are powered by electrical power that is delivered from the vehicle through the electrically conductive tether.

3. The system of claim 1, wherein when the aerial wing is operated in the powered flying mode, the rotors are powered by electrical power that is stored in a power storage device on the aerial wing.

4. The system of claim 1, wherein the aerial wing is also adapted to operate in a power generation mode during the flying mode where air moving across the rotatable blades of one or more of the rotors forces them to rotate, thereby driving a generator to produce electrical energy.

5. The system of claim 4, wherein at least some of the electrical energy produced during the power generation mode is delivered through the electrically conductive tether to the vehicle.

6. The system of claim 1, wherein the aerial wing provides a pulling force on the vehicle while in the flying mode or in the powered flying mode.

7. The system of claim 4, wherein the aerial wing is adapted to operate in the powered flying mode and the power generation mode at the same time, by operating one or more of the rotors so that the rotatable blades serve as thrust-generating propellers, and by operating one or more of the rotors in the power generation mode.

8. The system of claim 5, further comprising:
    an electrodialysis system arranged on the vehicle and configured to extract carbon dioxide ($CO_2$) from seawater;
    an electrolysis system arranged on the vehicle and configured to apply electrolysis to seawater to produce hydrogen ($H_2$);
    a refinery system configured to use both the $H_2$ produced by electrolysis system and the $CO_2$ extracted by the electrodialysis system to produce a fuel or chemical; and
    wherein electrical energy produced during power generation mode is adapted to provide power for at least one of the electrolysis system and the electrodialysis system.

9. The system of claim 8, wherein the refinery system is configured to:
    use both the $H_2$ produced by electrolysis system and the $CO_2$ extracted by the electrodialysis system to produce a synthetic fuel; and
    convert at least some of the synthetic fuel into ethanol.

10. The system of claim 1, further comprising:
    a rotatable drum positioned with the ground station;
    wherein rotation of the drum causes the tether to be wrapped around the drum causing the aerial wing to be reeled in towards the ground station; and
    wherein the tether may be reeled out from the rotatable drum when the aerial wing ascends.

11. The system of claim 10, further comprising:
    an aerial wing perch positioned with the ground station;

wherein the aerial wing is adapted to be parked on the aerial wing perch.

12. The system of claim 11, wherein the aerial wing is adapted to fly in a hover mode where a fuselage that is attached to the aerial wing is generally perpendicular to horizontal when the aerial wing is approaching or departing the aerial wing perch.

13. An airborne wind turbine system, comprising:
an aerial wing;
a plurality of rotors each having a plurality of rotatable blades positioned on the aerial wing;
an electrically conductive tether having a first end secured to the aerial wing and a second end secured to a ground station positionable on a vehicle;
wherein the aerial wing is adapted to receive electrical power from the vehicle that is delivered to the aerial wing through the electrically conductive tether;
wherein the aerial wing is adapted to (i) operate in a flying mode to harness wind energy to provide a first pulling force through the tether to pull the vehicle; (ii) and operate in a powered flying mode during cross-wind flight wherein the rotors may be powered so that the rotatable blades serve as thrust-generating propellers to provide a second pulling force through the tether to pull the vehicle; and
wherein the ground station is attached to the vehicle such that the aerial wing is adapted to operate in the powered flying mode to steer or turn the vehicle.

14. The system of claim 13, wherein the aerial wing is also adapted to operate in a power generation mode during the flying mode where air moving across the rotatable blades of one or more of the rotors forces them to rotate, thereby driving a generator to produce electrical energy.

15. The system of claim 14, wherein the aerial wing is adapted to operate in the powered flying mode and the power generation mode at the same time, by operating one or more of the rotors so that the rotatable blades serve as thrust-generating propellers, and by operating one or more of the rotors in the power generation mode.

16. A method of pulling a vehicle, comprising the steps of:
providing an aerial wing with a plurality of rotors each having a plurality of rotatable blades positioned on the aerial wing, and having an electrically conductive tether having a first end secured to the aerial wing and a second end secured to a ground station positioned on a vehicle, wherein the aerial wing is adapted to receive electrical power from the vehicle that is delivered to the aerial wing through the electrically conductive tether; wherein the aerial wing is adapted to operate in a flying mode to harness wind energy to provide a first pulling force through the tether to pull the vehicle; and wherein the aerial wing is also adapted to operate in a powered flying mode during cross-wind flight wherein the one or more of the rotors are powered so that the rotatable blades serve as thrust-generating propellers to provide a second pulling force through the tether to pull the vehicle; and wherein the ground station is positioned on the vehicle such that the aerial wing is adapted to operate in a powered flying mode to steer or turn the vehicle; and
operating the aerial wing in the powered flying mode to provide the second pulling force through the tether to pull the vehicle.

17. The method of claim 16, further including the step of operating the aerial wing in power generation mode during the powered flying mode where air moving across the rotatable blades of one or more of the rotors forces them to rotate, thereby driving a generator to produce electrical energy.

18. The method of claim 17, further including the step of delivering at least some of the electrical energy produced during the power generation mode through the electrically conductive tether to the vehicle.

19. The method of claim 16, further including the step of operating the aerial wing in power generation mode during the powered flying mode, by operating one or more of the rotors so that the rotatable blades serve as thrust-generating propellers, and by operating one or more of the rotors in the power generation mode where air moving across the rotatable blades of one or more of the rotors forces them to rotate, thereby driving a generator to produce electrical energy.

20. The method of claim 16, further including a rotatable drum positioned with the ground station wherein rotation of the drum causes the tether to be wrapped around the drum causing the aerial wing to be reeled in towards the ground station, wherein the tether may be reeled out from the rotatable drum when the aerial wing ascends, and an aerial wing perch positioned with the ground station wherein the aerial wing is adapted to be parked on the aerial wing perch.

21. The method of claim 20, further including the step of operating the aerial wing in a hover mode where a fuselage that is attached to the aerial wing is generally perpendicular to horizontal when the aerial wing is approaching the aerial wing perch.

22. The method of claim 20, further including the step of operating the aerial wing in a hover mode where a fuselage that is attached to the aerial wing is generally perpendicular to horizontal when the aerial wing is departing the aerial wing perch.

23. The method of claim 16, further including the step of operating the aerial wing in powered flying mode at an angle from a longitudinal axis of the vehicle to steer or turn the vehicle.

24. The method of claims 23, wherein the angle is between 45 and 135 degrees.

25. The method of claim 18, further including the steps of:
operating an electrodialysis system arranged on the vehicle to extract carbon dioxide ($CO_2$) from seawater;
operating an electrolysis system arranged on the vehicle to apply electrolysis to seawater to produce hydrogen ($H_2$);
operating a refinery system arranged on the vehicle to use both the $H_2$ produced by the electrolysis system and the $CO_2$ extracted by the electrodialysis system to produce a fuel or chemical; and
using electrical energy produced during power generation mode to provide power for at least one of the electrolysis system and the electrodialysis system.

26. The method of claim 25, further including the step of operating the refinery system to use both the $H_2$ produced by the electrolysis system and the $CO_2$ extracted by the electrodialysis system to produce a synthetic fuel.

27. The method of claim 26, further including the step of converting at least some of the synthetic fuel into ethanol.

* * * * *